(12) United States Patent
Conley et al.

(10) Patent No.: US 12,138,254 B2
(45) Date of Patent: Nov. 12, 2024

(54) CHRONIC NIGHTLY DOSING OF LASMIDITAN FOR MIGRAINE PREVENTION

(71) Applicant: Eli Lilly and Company, Indianapolis, IN (US)

(72) Inventors: Robert Russell Conley, Annapolis, MD (US); Gudarz Davar, Indianapolis, IN (US); Kirk Willis Johnson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 606 days.

(21) Appl. No.: 17/271,950

(22) PCT Filed: Sep. 3, 2019

(86) PCT No.: PCT/US2019/049340
§ 371 (c)(1),
(2) Date: Feb. 26, 2021

(87) PCT Pub. No.: WO2020/051137
PCT Pub. Date: Mar. 12, 2020

(65) Prior Publication Data
US 2021/0338655 A1   Nov. 4, 2021

Related U.S. Application Data

(60) Provisional application No. 62/726,585, filed on Sep. 4, 2018.

(51) Int. Cl.
*A61K 31/4545* (2006.01)
*A61K 9/00* (2006.01)
*A61P 25/06* (2006.01)

(52) U.S. Cl.
CPC ........ *A61K 31/4545* (2013.01); *A61K 9/0053* (2013.01); *A61P 25/06* (2018.01)

(58) Field of Classification Search
CPC ............................ A61K 31/4545; A61P 25/06
See application file for complete search history.

(56) References Cited

U.S. PATENT DOCUMENTS

| | | |
|---|---|---|
| 5,011,472 A | 4/1991 | Aebischer et al. |
| 5,023,252 A | 6/1991 | Hseih |
| 5,385,912 A | 1/1995 | Neuenschwander et al. |
| 5,521,196 A | 5/1996 | Audia et al. |
| 5,521,197 A | 5/1996 | Audia |
| 5,698,571 A | 12/1997 | Audia et al. |
| 5,708,008 A | 1/1998 | Audia et al. |
| 5,708,187 A | 1/1998 | Frlaugh et al. |
| 5,721,252 A | 2/1998 | Audia et al. |
| 5,814,653 A | 9/1998 | Flaugh et al. |
| 5,817,671 A | 10/1998 | Filla et al. |
| 6,528,529 B1 | 3/2003 | Brann et al. |
| 6,650,463 B2 | 11/2003 | Obikawa et al. |
| 6,777,428 B1 | 8/2004 | Krushinski, Jr. et al. |
| 7,291,632 B2 | 11/2007 | Blanco-Pillado et al. |
| 7,423,050 B2 | 9/2008 | Cohen et al. |
| 7,608,629 B2 | 10/2009 | Blanco-Pillado et al. |
| 8,044,207 B2 | 10/2011 | Mancuso et al. |
| 8,697,876 B2 | 4/2014 | Carniaux et al. |
| 8,748,459 B2 | 6/2014 | Cohen et al. |
| 2002/0175891 A1 | 11/2002 | Obikawa et al. |
| 2003/0144285 A1 | 7/2003 | Brann et al. |
| 2003/0175445 A1 | 9/2003 | Kirsch et al. |
| 2005/0009871 A1 | 1/2005 | Ramesh et al. |
| 2005/0080112 A1 | 4/2005 | Madsen et al. |
| 2006/0178349 A1 | 8/2006 | Plachetka |
| 2006/0211734 A1 | 9/2006 | Blanco-Pillado et al. |
| 2007/0129354 A1 | 6/2007 | Aston et al. |
| 2007/0219187 A1 | 9/2007 | Bessis et al. |
| 2007/0299110 A1 | 12/2007 | Gagliardi et al. |
| 2008/0300407 A1 | 12/2008 | Cohen et al. |
| 2010/0256187 A1 | 10/2010 | Pilgrim et al. |
| 2020/0087279 A1 | 3/2020 | Allieri et al. |
| 2020/0268735 A1 | 8/2020 | Aurora et al. |
| 2021/0401822 A1* | 12/2021 | Pilgrim .................. A61P 25/06 |

FOREIGN PATENT DOCUMENTS

| | | |
|---|---|---|
| EP | 1492786 B1 | 3/2003 |
| EP | 10759491.3 | 7/2018 |
| KR | 20060067738 A | 6/2006 |
| WO | 9314201 | 7/1993 |
| WO | 9629075 A1 | 9/1996 |
| WO | 9713512 A1 | 4/1997 |
| WO | 9808502 A1 | 3/1998 |
| WO | 9815545 A1 | 4/1998 |

(Continued)

OTHER PUBLICATIONS

Croop et al, NCT03732638, submitted Nov. 5, 2018, https://clinicaltrials.gov/study/NCT03732638?titles=NCT03732638&rank=1&a=33, p. 1-19 (Year: 2018).*
Peter J Goadsby et al, "Migraine—Current Understanding and Treatment", N. Engl. J. Med, vol. 346, No. 4, Jan. 24, 2002.
Markus Farkkifa et al, "Efficacy and tolerability of Lasmiditan, an oral 5-HT1F receptor agonist, for the acute treatment of migraine: a phase 2 randomised, placebo-controlled, parallel-group, dose-ranging study", Lancet Neurology, vol. 11, No. 5, May 1, 2012.
Anonymous, "Dose-ranging Study of Oral COL-144 in Acute Migraine Treatment", ClinicalTrials.gov, Sep. 10, 2009.
Jessica C Oswald, et al, "Lasmiditan for the treatment of acute migraine: a review and potential role in clinical practice", Journal of Pain Research, vol. 11, pp. 2221-2227, Oct. 8, 2018.
Berge et al. "Pharmaceutical Salts." J. Pharm. Sci 66.1(1977):1-19.
Ferrari et al. "Oral Triptans (Serotonin 5-HT1B/1D Agonists) in Acute Migraine Treatment: A Meta-Analysis of 53 Trials." Lancet. 358(2001):1668-1675.

(Continued)

*Primary Examiner* — Samantha L Shterengarts
*Assistant Examiner* — Karen Cheng
(74) *Attorney, Agent, or Firm* — Dan L. Wood

(57) ABSTRACT

The present invention relates to chronic nightly use of lasmiditan for the prevention of migraine, particularly therapy resistant migraine which is defined herein as migraine refractory to two or more prior monotherapy and/or dual therapy treatment or prevention regimens.

10 Claims, 4 Drawing Sheets

(56) References Cited

FOREIGN PATENT DOCUMENTS

| WO | 9820875 A1 | 5/1998 |
|---|---|---|
| WO | 9846570 A1 | 10/1998 |
| WO | 9855115 A1 | 12/1998 |
| WO | 9925348 A1 | 5/1999 |
| WO | 0000487 A1 | 1/2000 |
| WO | 0000490 A2 | 1/2000 |
| WO | 0034266 A1 | 6/2000 |
| WO | 0047559 A2 | 8/2000 |
| WO | 0050426 A2 | 8/2000 |
| WO | 200105763 A2 | 1/2001 |
| WO | 200206196 A1 | 1/2002 |
| WO | 2003000245 A1 | 1/2003 |
| WO | 03084949 A1 | 10/2003 |
| WO | 04047739 A2 | 6/2004 |
| WO | 2004089874 A1 | 10/2004 |
| WO | 2004099127 A1 | 11/2004 |
| WO | 2005007621 A2 | 1/2005 |
| WO | 2005044797 A1 | 5/2005 |
| WO | 2006048771 A1 | 5/2006 |
| WO | 2006058905 A1 | 6/2006 |
| WO | 2006081127 A2 | 8/2006 |
| WO | 2006108487 A1 | 10/2006 |
| WO | 08114971 A1 | 9/2008 |
| WO | 2010115125 A2 | 10/2010 |
| WO | 11123654 A1 | 10/2011 |

OTHER PUBLICATIONS

Goadsby et al. "Migraine—Current Understanding and Treatment." N. Engl J. Med. 346.4(2002):257-270.
Goldstein et al. "Selective Seratonin 1F (5-HT1F) Receptor Agonist LY334370 for Acute Migraine: A Randomised Conrolled Trial." Lancet. 358.9289(2001):1230-1234.
Graham et al. "Mechanism of Migraine Headache and Action of Ergotamine Tartrate." Arc. Neurol. Pyschaitry. 39.4(1938):737-763.
Gros et al. "Aggregative Activation in Heterocyclic Chemistry. Part 5. Lithiation of Pyrldine and Quinoline with the Complex Base BuLi-Me2N(CH2)2OLi (BuLi-LiDMAE)." J. Chem. Soc., Perkin Trans. 1.24(1997(:3597-3600.
Hall et al. "A Group Sequential Adaptive Treatment Assignment Design for Proof of Concept and Dose Selection in Headache Trials." Contemp. Clin. Trials. 26.3(2005):349-364.
Headache Classification Subcommittee of the International Headache Society. "The International Classification of Headache Disorders: Second Edition." Cephalalgia. 24.S11(2004):1-160.
Herrick-Davis et al. "Detection and Characterization of the Serotonin 5-HT 1D Receptor in Rat and Human Brain." J. Neurochem. 50.5(1988):1624-1631.
Ho et al. "Efficacy and Tolerability of MK-0974 (telcagepant), a New Oral Antagonist of Calcitonin Gene-Related Peptide Receptor, Compared with Zolmitriptan for Acute Migraine: A Randomised, Placebo-Controlled, Parallel-Treatment Trial." Lancet. 372. 9656(2008):2115-2123.
Humphrey et al. "Serotonin and Migraine." Ann. N.Y. Acad. Sci. 600(1990):587-598.
International Headache Society Clinical Trials Subcommittee. "Guidelines for Controlled Trials of Drugs in Migraine: Second Edition." Cephalalgia. 20.9(2000):765-786.
MaassenVanDenBrink et al. "Coronary Side-Effect Potential of Current and Prospective Antimigraine Drugs." Circulation. 98. 1(1998):25-30.
Moskowitz. "Interpreting Vessel Diameter Changes in Vascular Headaches." Cephalalgia. 12.1(1992):5-7.
Mostkowitz. "Neurogenic Inflammation in the Pathophysiology and Treatment of Migraine." Neurol. 43.S3(1993):S6-S20.
Nelson et al. COL-144: Preclinical Profile of a Selective 5-HT1F Receptor Agonist for Migraine. Cephalalgia. 29(2009):122-123. (Abstract # PC. 12).
Olesen et al. "Calcitonin Gene-Related Peptide Receptor Antagonist BIBN 4096 BS for the Acute Treatment of Migraine." N. Engl. J. Med. 350.11(2004):1404-1110.
Schoonman et al. "Migraine Headache is not Associated with Cerebral of Meningeal Vasodilation—a 3 T Magnetic Resonance Angioraphy Study." Brain. 131.Pt8(2008):2192-2200.
Stovner et al. "The Global Burden of Headache: A Documentation of Headache Prevalence and Disability Worldwide." Cephalalgia. 27.3(2007)193-210.
Visser et al. "Chest Symptoms After Sumatriptan: A Two-Year Clinical Practice Review in 735 Consecutive Migraine Patients." Cephalalgia. 16.8(1996):554-559.
Weinshank et al. "Human Serotonin 1D Receptor is Encoded by a Subfamily of Two Distinct Genes: 5-HT1Da and 5-HT1DB." PNAS. 89.8(1992):3630-3634.
Welch et al. "Tolerability of Sumatriptan: Clinical Trials and Post-Marketing Experience." Cephalalgia. 20.8(2000):687-695.
Adham et al., "Cloning of another human serotonin receptor (5-HT1F): A Fifth 5-HT1 receptor subtype coupled to the inhibition of adenylate cyclase", Proc. Natl. Acad. Sci. U.S.A., 90:408-412 (1993).
"Dose-ranging Study of Oral COL-144 in Acute Migraine Treatment—Study 1 of 2 for search of: Colucid", Clinical Trials, Apr. 16, 2009 (5 pages).
King, F. D., "Bioisosteres, Conformational Restriction, and Pro-drugs—Case History: An Example of a Conformational Restriction Approach", in Medicinal Chemistry: Principles and Practice, Royal Society of Chemistry, Cambridge, England, Ch. 14, pp. 206-209 (1994).
Phebus et al., "Characterization of LY344864 as a Pharmacological Tool to Study 5-HT1F Receptors: Binding Affinities, Brain Penetration and Activity in the Neurogenic Dural Inflammational Model of Migraine", Life Sciences, 6(21), 2117-2126 (1997) (Abstract Only).
Radl et al., "Synthesis and Antinociceptive Activity of Some 3-Chlorophenyl-and 6-Chloro-2-Pyridinyl Derivatives", Coll. Czech. Che,. Comm., 64(2):377-388 (1999) (Abstract Only).
Cephalalgia 2009, 29, 122-123 "Abstracts of the European Headache and Migraine Trust International Congress 2008, Sep. 4-7, 2008, abstract PC.12 of Nelson entitled COL-144: Preclinical profile of a selective 5-HT1F receptor agonist for migraine" (D3a) and related poster (D3b).
Cephalalgia 2009, 29, 122-123 "Abstracts of the European Headache and Migraine Trust International Congress 2008, Sep. 4-7, 2008, abstract PC.11 of Reuter entitled COL-144, a selective 5-HT1F agonist, for the treatment of migraine attacks" (D4a) and related poster (D4b).
Press release of CoLucid Pharmaceuticals Inc. entitled "Phase II Results of COL-144 Presented at European Headache and Migraine Trust International Congress 2008", Sep. 6, 2008.
Drug Data Report 2009, 31(10), 964.
Cephalalgia 29 (Suppl. 1) (2009) 24-25 "14th Congress of the International Headache Society Sep. 10-13, 2009, Philidelphia, PA", abstract PO33 of Liefaard entitled "Prediction of therapeutically effective dose of OL-144 based on relationship between plasma concentrations and headache response" (D7a) and related poster (D7b).
Cephalalgia 29 (Suppl. 1) (2009) 24-25 "14th Congress of the International Headache Society Sep. 10-13, 2009, Philidelphia, PA", abstract PO34 of Pilgrim entitled "COL-144, an orally bioavailable selective 5-HT1F receptor agonist for acute migraine therapy" (D8a) and related poster (D8b).
Clinical trial record NCT00883051 as stored in the internet archive on 08.09.209.
WHO Drug Information, vol. 23, No. 4, 2009, 322-323.
EMEA "Note for guidance on general considerations for clinical trials", Mar. 1998.
Reuter et al., "COL-144: A Selective 5-HT1F Agonist For the Treatment of Migraine Attacks" Cephalalgia, vol. 29, Jan. 2009.
Information about publication date of Reuter et al. (2009) Cephalalgia, 29(1):101-178.
U.S. National Library of Medicine, "Dose-ranging Study of Oral COL-144 in Acute Migraine Treatment" Apr. 16, 2009.

(56) References Cited

OTHER PUBLICATIONS

Lancet Neurol 2012; 11: 405-13, Färkkilä, M. et al., Efficacy and tolerability of lasmiditan, an oral 5-HT1F receptor agonist, for the acute treatment of migraine: a phase 2 randomised, placebo-controlled, parallel-group, dose-ranging study.

International Searching Authority, International Search Report, and Search Strategy for PCT/US2019/049340, WO, A1, Sep. 3, 2019, Eli Lilly and Company.

Written Opinion of the International Searching Authority for PCT/US2019/049340, WO, A1, Sep. 3, 2019, Eli Lilly and Company.

Notice of opposition to a European patent issued for European Patent No. 3846810, dated Jul. 15, 2024, filed by Teva Pharmaceutical Industries, Ltd., 23 pages. EP, Jul. 15, 2024, Eli Lilly and Cpmpany.

Communication of a notice of opposition issued for European Patent No. 3846810, issued on Jul 18, 2024, filed by Teva Pharmaceutical Industries, Ltd., 24 pages. EP, Jul. 18, 2024, Eli Lilly and Company.

Consolidated list of reference documents presented in Notice of opposition to a European patent issued for European Patent No. 3846810, dated Jul. 15, 2024, filed by Teva Pharmaceutical Industries, Ltd., 125 pages.

Färkkilä et al., "Lasmiditan (col. 144) a Selective 5-HT1F Agonist, is a Rapid & Effective Oral Treatment for Acute Migraine", 2012 or earlier, CoLucid Pharmaceuticals, Inc., https://web.archive.org/web/20120514060922/http://www.colucid.com/pdf/2010_ehmitic_ph2_oral_poster.pdf.

Garza et al., "Prophylaxis of migraine", Neuropsychiatric Disease and Treatment, 2006, vol. 2(3), pp. 281-291.

\* cited by examiner

Schema:

[a] In addition to the daily patient eDiary, patients will complete a paper log.

[b] Visit 801 will be a phone visit to assess any withdrawal symptoms and adverse events associated with the study treatment.

CHRONIC NIGHTLY DOSING OF LASMIDITAN FOR MIGRAINE PREVENTION

The present invention relates to chronic nightly administration of lasmiditan to prevent migraine, particularly to prevent therapy resistant migraine which is defined herein as migraine refractory to two or more prior monotherapy and/or dual therapy migraine treatment or prevention regimens. The methods of the present invention provide novel means to modify the disease state of patients with recurrent migraine, and thereby reduce the patients' susceptibility to having recurrent migraines. Thus, the present methods for disease modification by chronic dosing of lasmiditan provide a safe, tolerable, effective and convenient oral means to prevent migraines, and restore patients functioning to a relatively migraine disease-free state.

Migraine is a serious, chronic, and disabling neurological disease characterized by attacks of moderate to severe headache pain associated with other bothersome symptoms. Migraine attacks typically last from 4 to 72 hours if untreated or unsuccessfully treated. People with migraine may experience an aura prior to the onset of their headache, and attacks can be exacerbated by even minor physical activity. In addition, people with migraine have higher lifetime rates of comorbid depression, anxiety, panic disorder, sleep disturbances, chronic pain syndromes, and suicide attempts, and are at higher risk for ischemic stroke and other cardiovascular disease. The prevalence of migraine in the United States and Western Europe ranges from 11% to 12%, with higher rates among women (16% to 18%) than men (6% to 7%). The disease is particularly common among individuals between the ages of 25 and 55 years, and the burden is considerable for both patients and the society. People with migraine report that pain is the most intense and disabling symptom during an attack, while other burdensome symptoms include photophobia, phonophobia, nausea, and vomiting. Among those with frequent migraine attacks, 78% reported not being fully functioning at their jobs, with 15 days of reduced productivity at work or school in a 3-month period. Research indicates that approximately 90% of people with migraine have a reduced ability to function, and approximately 33% require bed rest during migraine attacks. Migraine has been reported to be the second highest cause of years lost due to disability, interfering significantly with occupational, educational, household, family, and social responsibilities.

The available treatment options for migraine have unsatisfactory rates of efficacy, tolerability and patient adherence. In the 2013 Global Burden of Disease Study, migraine accounted for over half of all years lost to disability that were attributed to neurological disorders (*New strategies for the treatment and prevention of primary headache disorders*, N. M. Schuster & A. M. Rapoport, Nature Reviews Neurology (2016) 12, 635-650). While patients with relatively infrequent migraine attacks (for example, occurring once or twice monthly) generally manage their individual attacks by taking medication for acute treatment only when needed, patients with more frequent migraine attacks often are treated with preventive drugs. Four approved oral drugs are currently available for migraine prevention in the US: propranolol, timolol, divalproex sodium, and topiramate. Despite the availability of some oral options for preventive treatment, many patients have poor response or tolerability issues, and an analysis of individuals taking an oral migraine preventive showed poor adherence with only 26% to 29% remaining on drug at 6 months, and 17% to 20% remained on drug at 12 months. Therefore, substantial need remains for alternative orally administered efficacious and well-tolerated agents that can reduce migraine frequency and improve patient functioning.

Lasmiditan is a selective and highly potent $5\text{-HT}_{1F}$ receptor agonist which is in development for acute on-demand treatment of migraine (See e.g. Rubio-Beltrin et al., Pharmacol Ther 2018; 186:88-97, and *Lasmiditan for the Treatment of Migraine*, Capi, M. et al., Expert Opinion Investigational Drugs, (2017), Vol. 26, NO. 2, 227-234). Lasmiditan (COL 144, LY 573144, CAS Registry No. 439239-90-4) can be described chemically as 2,4,6-trifluoro-N-[6-(1-methyl-piperidin-4-ylcarbonyl)-pyridin-2-yl]-benzamide and can be structurally represented as follows:

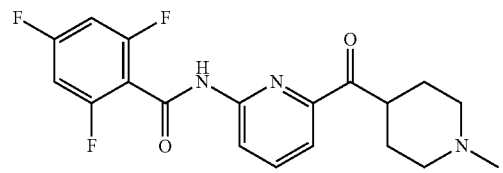 [SMILES: CN1CCC(C(=O)c2cccc(NC(=O)c3c(F)cc(F)cc3F)n2)CC1]

Prior clinical development studies of lasmiditan have employed acute on-demand treatment regimens to relieve migraine pain and symptoms and treat migraine. See for instance, *Phase 3 Studies (SAMURAI, SPARTAN) of Lasmiditan Compared to Placebo for Acute Treatment of Migraine* (S50.008), Linda A. Wietecha, Bernice Kuca, Josephine Asafu-Adjei, Sheena K. Aurora, Neurology April 2018, 90 (15 Supplement) S50.008; where the authors have reported that at 2 hours post-first dose, significantly greater proportions of patients ($p<0.001$) were headache pain-free (lasmiditan 200 mg: SAMURAI 32.2%, SPARTAN 38.8%; placebo: SAMURAI 15.3%, SPARTAN 21.3%) and most bothersome symptom (MBS)-free (lasmiditan 200 mg: SAMURAI 40.7%, SPARTAN 48.7%; placebo: SAMURAI 29.5%, SPARTAN 33.5%) with lasmiditan 200 mg compared with placebo. For both endpoints, significance was also noted for other lasmiditan dose groups (100 mg, 50 mg) compared to placebo. The most frequently reported TEAEs with lasmiditan (≥2% and greater than placebo) after the first dose were dizziness, paresthesia, somnolence, fatigue, nausea, and lethargy, and most events were mild-to-moderate in severity. From this analysis, the authors concluded the primary and key secondary endpoints were met and safety outcomes were consistent across the two Phase 3 studies. Thus, acute on-demand use of lasmiditan provides effective treatment for a substantial population of migraine patients, however some patients may continue to have attacks and improved methods of treating and/or preventing these attacks represent an important therapeutic goal.

The management of patients with migraine is often unsatisfactory because available acute and preventive therapies are either ineffective or poorly tolerated. The acute treatment of migraine attacks has been limited to the use of analgesics, combinations of analgesics with caffeine, ergotamines, and the triptans. Despite the availability of certain preventive medications for migraine, many patients do not respond to these treatments or are unable to tolerate them. (For a description of such agents see e.g. *New Therapeutic Approaches for the Prevention and Treatment of Migraine*, Diener, H. C. et al., (2015) Lancet Neurology, 14:1010-22). In countries like the United States, Germany, France, and Japan, approximately 43% of patients have experienced a failure of their preventive medication or have switched treatments. Among patients with episodic or chronic migraine who are undergoing oral preventative treatment, side effects and a lack of efficacy are the most common reasons for discontinuing their treatment. Prior treatments of migraine may leave significant numbers of patients without adequate treatment. For instance, up to 40% of migraine attacks, ~30% of patients, fail to respond to a particular triptan, because of suboptimal efficacy or tolerability issues (See Dodick D W. Headache. 2005; 45:156-162, and Tepper D E. Headache. 2013(53)577-578). Because of their vasoconstricting effects, these medications may have contraindications, warnings, and precautions for patients with cardiovascular risk factors and disease (See Alwhaibi M, et al. Pain Res Treat. 2016; 2016:8538101, and Gilmore B, Michael M. Am Fam Physician. 2011(83)271-280). Thus, for prior monotherapy or dual therapy migraine prevention and/or treatments, a substantial fraction of patients may fail to achieve headache relief and/or freedom from pain in response to treatment or preventative therapy. Further, some patients, referred to herein as therapy resistant migraine patients, will fail to successfully manage their migraine attacks and will suffer from migraines which are refractory to two or more prior monotherapy and/or dual therapy prevention or treatment regimens. These inadequately controlled migraine patients may have a number of migraine days per-month that continues to be significantly disabling.

There exists a need for more and different therapies that may prove to be effective in preventing migraine, and/or reducing the patients' susceptibility to migraine, and in particular for the prevention of therapy resistant migraines. Therapy resistant migraines is defined herein as migraine refractory to two or more prior monotherapy and/or dual therapy prevention and/or treatment regimens. Thus, there exists a need for new prevention options for patients who suffer from migraine attacks and have previously failed migraine preventative medications.

The present invention provides for chronic nightly administration of lasmiditan and methods of preventing migraine. Chronic nightly administration of lasmiditan represents an innovative approach for prevention of migraine by selectively targeting 5-HT$_{1F}$ with long-term nightly administration targeted to coincide with patients sleeping hours. Further, the present invention provides for the use of chronic nightly administration of lasmiditan for reducing the patients' susceptibility to migraine. Further, the present invention provides for chronic nightly administration of lasmiditan and to methods of preventing therapy resistant migraine, which is defined herein as migraine refractory to two or more prior monotherapy and/or dual therapy treatment or prevention regimens.

Preclinical studies such as those described in Example 1 suggest that lasmiditan use can induce a surprisingly persistent improvement in a dysfunctional state of the trigeminal nervous system. Similarly, phase III clinical studies such as those described in Example 2 provide surprising and unexpected evidence that improvements in migraine patients susceptibility to migraine attacks may accrue over time with extended periods of on-demand lasmiditan use. These studies have led to the concept that chronic nightly administration of lasmiditan will provide an improved means to reduce migraine patients' susceptibility to migraine, and/or prevent the patients' migraines in a clinically advantageous manner. The present invention provides for the chronic nightly administration of lasmiditan such that the migraine patient will have 8 hours, and more preferably 12 hours, between the time of administration and the next window of time wherein the patient will desire to drive an automobile or engage in comparable activities. This regimen is advantageous because lasmiditan treatment can be associated with mild-to-moderate dizziness, paresthesia, somnolence, fatigue, nausea, and lethargy, and as a result, patients may need to avoid driving for certain times following administration. In addition, the present invention provides for the chronic nightly administration of lasmiditan such that the migraine patient will further be able to employ either lower or higher doses of lasmiditan, such that effective prevention is achieved for the individual patient. In particular the present invention provides for the chronic nightly administration of lasmiditan, preferably using a total dose per administration of 25 mg to 200 mg per night.

Accordingly, the present invention provides chronic nightly administration of lasmiditan for reducing the patients' susceptibility to migraine, and/or prevention of migraine, and in particular for the prevention of therapy resistant migraines. Methods of chronic nightly administration of lasmiditan for reducing the patients' susceptibility to migraine, and/or prevention of migraine, and in particular for the prevention of therapy resistant migraines, employ certain doses and dosing regimens for administration of lasmiditan which are described below.

The present invention provides chronic nightly administration of lasmiditan for reducing the patients' susceptibility to migraine, and/or prevention of migraine, and in particular for the prevention of therapy resistant migraines, comprising administration of a total nightly dose of 25-200 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 25 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 50 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 75 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 100 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 150 mg lasmiditan, or a pharmaceutically acceptable salt thereof, such as the hemisuccinate salt, and a pharmaceutically acceptable diluent or carrier.

The present invention provides chronic nightly administration of lasmiditan for reducing the patients' susceptibility to migraine, and/or prevention of migraine, and in particular for the prevention of therapy resistant migraines, comprising administration of a total nightly dose of 200 mg lasmiditan, or a pharmaceutically acceptable salt thereof, such as the hemisuccinate salt, and a pharmaceutically acceptable diluent or carrier.

The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly, for at least five consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly, for at least thirty consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly, every other night for at least ten consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly, every other night for at least thirty consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine wherein the compound, or pharmaceutically acceptable salt thereof, is chronically administered nightly, wherein the patients' migraines have been refractory to two or more prior monotherapy and/or dual therapy treatment and/or prevention regimens. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg to 200 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 50 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 75 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 100 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 150 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 200 mg.

The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine, wherein the compound, or pharmaceutically acceptable salt thereof, is orally administered nightly in a dose of 25-200 mg per dose. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine, wherein the compound, or pharmaceutically acceptable salt thereof, is orally administered nightly in a dose of 25-200 mg per dose, for at least five consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine, wherein the compound, or pharmaceutically acceptable salt thereof, is orally administered nightly in a dose of 25-200 mg per dose, for at least thirty consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine, wherein the compound, or pharmaceutically acceptable salt thereof, is orally administered nightly in a dose of 25-200 mg per dose, every other night for at least ten consecutive nights. The present invention provides the compound 2,4,6-trifluoro-N-[6-(1-methyl-piperidin-4-ylcarbonyl)-pyridin-2-yl]-benzamide, or a pharmaceutically acceptable salt thereof, for use in the prevention of migraine, wherein the compound, or pharmaceutically acceptable salt thereof, is orally administered nightly in a dose of 25-200 mg per dose, every other night for at least thirty consecutive nights. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 50 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 75 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 100 mg. A use according to any one of the embodiments above, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 150 mg. A use according to any one of the embodiments above, wherein 2,4,6- trifluoro-N-[6-(1-methyl-piperidin-4-ylcarbonyl)-pyridin-2-yl]-benzamide, or a pharmaceutically acceptable salt thereof, is administered at a dose of 200 mg.

The present invention provides for the chronic nightly administration of lasmiditan, comprising administration of a pharmaceutical composition of lasmiditan, wherein said composition is for oral administration and the amount of lasmiditan or pharmaceutically acceptable salt thereof is from about 25 mg to about 200 mg per dose. The present invention provides for the chronic nightly administration of a pharmaceutical composition of lasmiditan, wherein said composition is for buccal, sublingual, nasal/intranasal, transdermal, subcutaneous, injectable, intravenous, or intramuscular administration and the amount of lasmiditan or pharmaceutically acceptable salt thereof administered is from about 25 to about 200 mg per dose. The present invention provides for the chronic nightly administration of lasmiditan comprising administration of a pharmaceutical composition of lasmiditan, wherein said composition is for oral administration and the amount of lasmiditan or pharmaceutically acceptable salt thereof is from about 25 mg to about 100 mg per dose. The present invention provides for the chronic nightly administration of lasmiditan comprising administration of a pharmaceutical composition of lasmiditan, wherein said composition is for oral administration and the amount of lasmiditan or pharmaceutically acceptable salt thereof is from about 100 mg to about 200 mg per dose. The present invention provides for the chronic nightly administration of lasmiditan comprising administration of a pharmaceutical composition of lasmiditan, wherein the amount of lasmiditan is 25 mg per dose. The present invention provides for the chronic nightly administration of lasmiditan comprising administration of a pharmaceutical composition of lasmiditan, wherein the amount of lasmiditan is 50 mg per dose. The present invention provides for the chronic nightly administration of lasmiditan comprising administration of a pharmaceutical composition of lasmiditan, wherein the amount of lasmiditan is 75 mg per dose. The present invention provides for the chronic nightly administration of lasmiditan comprising administration of a pharmaceutical composition of lasmiditan, wherein the amount of lasmiditan is 100 mg per dose. The present invention provides for the chronic nightly administration of lasmiditan comprising administration of a pharmaceutical composition of lasmiditan, wherein the amount of lasmiditan is 150 mg per dose. The present invention provides for the chronic nightly administration of lasmiditan comprising administration of a pharmaceutical composition of lasmiditan, wherein the amount of lasmiditan is 200 mg per dose.

The present invention provides for the chronic nightly administration of a pharmaceutical composition of lasmiditan wherein the composition comprises the hemi-succinate salt of lasmiditan. The present invention provides for the chronic nightly administration of a pharmaceutical composition of lasmiditan wherein the composition comprises the hemi-succinate salt of lasmiditan and the amount administered is 25 mg per dose. The present invention provides for the chronic nightly administration of a pharmaceutical composition of lasmiditan wherein the composition comprises the hemi-succinate salt of lasmiditan and the amount administered is 50 mg per dose. The present invention provides for the chronic nightly administration of a pharmaceutical composition of lasmiditan wherein the composition comprises the hemi-succinate salt of lasmiditan and the amount administered is 75 mg per dose. The present invention provides for the chronic nightly administration of a pharmaceutical composition of lasmiditan wherein the composition comprises the hemi-succinate salt of lasmiditan and the amount administered is 100 mg per dose. The present invention provides for the chronic nightly administration of a pharmaceutical composition of lasmiditan wherein the composition comprises the hemi-succinate salt of lasmiditan and the amount administered is 150 mg per dose. The present invention provides for the chronic nightly administration of a pharmaceutical composition of lasmiditan wherein the composition comprises the hemi-succinate salt of lasmiditan and the amount administered is 200 mg per dose.

In one embodiment the invention provides a method for chronic nightly use of lasmiditan in the prevention of migraine in a patient. In another embodiment the invention provides a method for chronic nightly use of lasmiditan in the prevention of migraine in a patient, wherein lasmiditan is administered at a dose of 25 mg to 200 mg. In another embodiment the invention provides a method for chronic nightly use of lasmiditan in the prevention of migraine in a patient, wherein lasmiditan is administered at a dose of 25 mg. In another embodiment the invention provides a method for chronic nightly use of lasmiditan in the prevention of migraine in a patient, wherein lasmiditan is administered at a dose of 50 mg. In another embodiment the invention provides a method for chronic nightly use of lasmiditan in the prevention of migraine in a patient, wherein lasmiditan is administered at a dose of 75 mg. In another embodiment the invention provides a method for chronic nightly use of lasmiditan in the prevention of migraine in a patient, wherein lasmiditan is administered at a dose of 100 mg. In another embodiment the invention provides a method for chronic nightly use of lasmiditan in the prevention of migraine in a patient, wherein lasmiditan is administered at a dose of 150 mg. In another embodiment the invention provides a method for chronic nightly use of lasmiditan in the prevention of migraine in a patient, wherein lasmiditan is administered at a dose of 200 mg.

In another embodiment the invention provides a method for chronic nightly use of lasmiditan in the prevention of migraine in a patient, for at least five consecutive nights. In another embodiment the invention provides a method for chronic nightly use of lasmiditan in the prevention of migraine in a patient, for at least five consecutive nights, wherein lasmiditan is administered at a dose of 25 mg to 200 mg. In another embodiment the invention provides a method for chronic nightly use of lasmiditan in the prevention of migraine in a patient, for at least five consecutive nights, wherein lasmiditan is administered at a dose of 25 mg. In another embodiment the invention provides a method for chronic nightly use of lasmiditan in the prevention of migraine in a patient, for at least five consecutive nights, wherein lasmiditan is administered at a dose of 50 mg. In another embodiment the invention provides a method for chronic nightly use of lasmiditan in the prevention of migraine in a patient, for at least five consecutive nights, wherein lasmiditan is administered at a dose of 75 mg. In another embodiment the invention provides a method for chronic nightly use of lasmiditan in the prevention of migraine in a patient, for at least five consecutive nights, wherein lasmiditan is administered at a dose of 100 mg. In another embodiment the invention provides a method for chronic nightly use of lasmiditan in the prevention of migraine in a patient, for at least five consecutive nights, wherein lasmiditan is administered at a dose of 150 mg. In another embodiment the invention provides a method for chronic nightly use of lasmiditan in the prevention of migraine in a patient, for at least five consecutive nights, wherein lasmiditan is administered at a dose of 200 mg.

In another embodiment the invention provides a method for chronic nightly use of lasmiditan in the prevention of migraine in a patient, for at least thirty consecutive nights. In another embodiment the invention provides a method for chronic nightly use of lasmiditan in the prevention of migraine in a patient, for at least thirty consecutive nights, wherein lasmiditan is administered at a dose of 25 mg to 200 mg. In another embodiment the invention provides a method for chronic nightly use of lasmiditan in the prevention of migraine in a patient, for at least thirty consecutive nights, wherein lasmiditan is administered at a dose of 25 mg. In another embodiment the invention provides a method for chronic nightly use of lasmiditan in the prevention of migraine in a patient, for at least thirty consecutive nights, wherein lasmiditan is administered at a dose of 50 mg. In another embodiment the invention provides a method for chronic nightly use of lasmiditan in the prevention of migraine in a patient, for at least thirty consecutive nights, wherein lasmiditan is administered at a dose of 75 mg. In another embodiment the invention provides a method for chronic nightly use of lasmiditan in the prevention of migraine in a patient, for at least thirty consecutive nights, wherein lasmiditan is administered at a dose of 100 mg. In another embodiment the invention provides a method for chronic nightly use of lasmiditan in the prevention of migraine in a patient, for at least thirty consecutive nights, wherein lasmiditan is administered at a dose of 150 mg. In another embodiment the invention provides a method for chronic nightly use of lasmiditan in the prevention of migraine in a patient, for at least thirty consecutive nights, wherein lasmiditan is administered at a dose of 200 mg.

In another embodiment the invention provides a method for chronic nightly use of lasmiditan every other night in the prevention of migraine in a patient, for at least ten nights. In another embodiment the invention provides a method for chronic nightly use of lasmiditan every other night in the prevention of migraine in a patient, for at least ten nights, wherein lasmiditan is administered at a dose of 25 mg to 200 mg. In another embodiment the invention provides a method for chronic nightly use of lasmiditan every other night in the prevention of migraine in a patient, for at least ten nights, wherein lasmiditan is administered at a dose of 25 mg. In another embodiment the invention provides a method for chronic nightly use of lasmiditan every other night in the prevention of migraine in a patient, for at least ten nights, wherein lasmiditan is administered at a dose of 50 mg. In another embodiment the invention provides a method for chronic nightly use of lasmiditan every other night in the prevention of migraine in a patient, for at least ten nights, wherein lasmiditan is administered at a dose of 75 mg. In another embodiment the invention provides a method for chronic nightly use of lasmiditan every other night in the prevention of migraine in a patient, for at least ten nights, wherein lasmiditan is administered at a dose of 100 mg. In another embodiment the invention provides a method for chronic nightly use of lasmiditan every other night in the prevention of migraine in a patient, for at least ten nights, wherein lasmiditan is administered at a dose of 150 mg. In another embodiment the invention provides a method for chronic nightly use of lasmiditan every other night in the prevention of migraine in a patient, for at least ten nights, wherein lasmiditan is administered at a dose of 200 mg.

In another embodiment the invention provides a method for chronic nightly use of lasmiditan every other night in the prevention of migraine in a patient, for at least thirty nights. In another embodiment the invention provides a method for chronic nightly use of lasmiditan every other night in the prevention of migraine in a patient, for at least thirty nights, wherein lasmiditan is administered at a dose of 25 mg to 200 mg. In another embodiment the invention provides a method for chronic nightly use of lasmiditan every other night in the prevention of migraine in a patient, for at least thirty nights, wherein lasmiditan is administered at a dose of 25 mg. In another embodiment the invention provides a method for chronic nightly use of lasmiditan every other night in the prevention of migraine in a patient, for at least thirty nights, wherein lasmiditan is administered at a dose of 50 mg. In another embodiment the invention provides a method for chronic nightly use of lasmiditan every other night in the prevention of migraine in a patient, for at least thirty nights, wherein lasmiditan is administered at a dose of 75 mg. In another embodiment the invention provides a method for chronic nightly use of lasmiditan every other night in the prevention of migraine in a patient, for at least thirty nights, wherein lasmiditan is administered at a dose of 100 mg. In another embodiment the invention provides a method for chronic nightly use of lasmiditan every other night in the prevention of migraine in a patient, for at least thirty nights, wherein lasmiditan is administered at a dose of 150 mg. In another embodiment the invention provides a method for chronic nightly use of lasmiditan every other night in the prevention of migraine in a patient, for at least thirty nights, wherein lasmiditan is administered at a dose of 200 mg.

In another embodiment the invention provides a method for chronic nightly use of lasmiditan in the prevention of migraine in a patient, wherein the patients' migraines have been refractory to two or more prior monotherapy and/or dual therapy treatment and/or prevention regimens. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 25 mg to 200 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 25 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 50 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 75 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 100 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 150 mg. In another embodiment the invention provides a method for chronic nightly use of lasmiditan in the prevention of migraine in a patient, wherein the patients' migraines have been refractory to two or more prior monotherapy and/or dual therapy treatment and/or prevention regimens, wherein lasmiditan is administered at a dose of 200 mg.

The present invention provides a method for the prevention of migraine, in a patient in need thereof, comprising nightly administering to the patient 25-200 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 25 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 50 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 75 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 100 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 150 mg per oral dose of 2,4,6-trifluoro-N-[6-(1-methyl-piperidin-4-ylcarbonyl)-pyridin-2-yl]-benzamide, or a pharmaceutically acceptable salt thereof. The present invention provides a method for the prevention of migraine, in a patient in need thereof, comprising nightly administering to the patient 200 mg per oral dose of 2,4,6-trifluoro-N-[6-(1-methyl-piperidin-4-ylcarbonyl)-pyridin-2-yl]-benzamide, or a pharmaceutically acceptable salt thereof.

The present invention provides a method for the prevention of migraine, in a patient in need thereof, comprising nightly administering to the patient 25-200 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 25 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 50 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 75 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 100 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 150 mg per oral dose of lasmiditan, or a pharmaceutically acceptable salt thereof, and a pharmaceutically acceptable diluent or carrier. The present invention provides a method for the prevention of migraine, in a patient in need thereof, comprising nightly administering to the patient 200 mg per oral dose of lasmiditan, or a pharmaceutically acceptable salt thereof, and a pharmaceutically acceptable diluent or carrier.

The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of migraine in a patient. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of migraine in a patient, for at least five consecutive nights. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of migraine in a patient, for at least thirty consecutive nights. The present invention provides a method for chronic use of 2,4,6-trifluoro-N-[6-(1-methyl-piperidin-4-ylcarbonyl)-pyridin-2-yl]-benzamide, or a pharmaceutically acceptable salt thereof, every other night in the prevention of migraine in a patient, for at least ten nights. The present invention provides a method for chronic use of 2,4,6-trifluoro-N-[6-(1-methyl-piperidin-4-ylcarbonyl)-pyridin-2-yl]-benzamide, or a pharmaceutically acceptable salt thereof, every other night in the prevention of migraine in a patient, for at least thirty nights. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of migraine in a patient, wherein the patients' migraines have been refractory to two or more prior monotherapy and/or dual therapy treatment and/or prevention regimens. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg to 200 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 50 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 75 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 100 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 150 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 200 mg.

The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of cluster headache in a patient. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of cluster headache in a patient, for at least five consecutive nights. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of cluster headache in a patient, for at least thirty consecutive nights. The present invention provides a method for chronic use of 2,4,6-trifluoro-N-[6-(1-methyl-piperidin-4-ylcarbonyl)-pyridin-2-yl]-benzamide, or a pharmaceutically acceptable salt thereof, every other night in the prevention of cluster headache in a patient, for at least ten nights. The present invention provides a method for chronic use of 2,4,6-trifluoro-N-[6-(1-methyl-piperidin-4-ylcarbonyl)-pyridin-2-yl]-benzamide, or a pharmaceutically acceptable salt thereof, every other night in the prevention of cluster headache in a patient, for at least thirty nights. The present invention provides a method for chronic nightly use of 2,4,6-trifluoro-N-[6-(1-methyl-piperidin-4-ylcarbonyl)-pyridin-2-yl]-benzamide, or a pharmaceutically acceptable salt thereof, in the prevention of cluster headache in a patient, wherein the patients' migraines have been refractory to two or more prior monotherapy and/or dual therapy treatment and/or prevention regimens. The present invention provides a method of any one of claims 1 to 6, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg to 200 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 25 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 50 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 75 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 100 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 150 mg. The present invention provides a method of any one of the preceding embodiments, wherein 2,4,6-trifluoro-N-[6-(1-methyl-piperidin-4-ylcarbonyl)-pyridin-2-yl]-benzamide, or a pharmaceutically acceptable salt thereof, is administered at a dose of 200 mg.

The present invention provides a method for the prevention of migraine, in a patient in need thereof, comprising nightly administering to the patient 25-200 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 25 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 50 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 75 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 100 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 150 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 200 mg per oral dose of lasmiditan, or a pharmaceutically acceptable salt thereof, and a pharmaceutically acceptable diluent or carrier, for at least five consecutive nights.

The present invention provides a method for the prevention of migraine, in a patient in need thereof, comprising nightly administering to the patient 25-200 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 25 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 50 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 75 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 100 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 150 mg per oral dose of lasmiditan, or a pharmaceutically acceptable salt thereof, and a pharmaceutically acceptable diluent or carrier, for at least thirty consecutive nights.

The present invention provides a method for the prevention of migraine, in a patient in need thereof, comprising nightly administering to the patient 200 mg per oral dose of lasmiditan, or a pharmaceutically acceptable salt thereof, and a pharmaceutically acceptable diluent or carrier, for at least thirty consecutive nights.

While many patients will be able to successfully manage migraine episodes by treatment with lasmiditan on-demand, a population of patients may fail to successfully manage their migraine attacks with this treatment. Similarly, many patients may be able to prevent their migraines with a CGRP antagonist or another monotherapy for prevention. Yet, for a significant population, neither of these approaches will sufficiently prevent or manage their migraine disease, and these patients may have a number of migraine day's per-month that continues to be significantly disabling. Further, some patients, referred to herein as therapy resistant migraine patients, will fail to successfully prevent or manage their migraine attacks, and will suffer from migraines which are refractory to two or more prior monotherapy and/or dual therapy treatment and/or prevention regimens.

As defined herein, therapy resistant migraine patients will be those that continue to suffer from 3 or more migraine days per month despite two or more prior monotherapy and/or dual therapy treatment and/or prevention regimens. As used herein, two or more prior monotherapy and/or dual therapy treatment and/or prevention regimens means prior unsatisfactory treatment attempts with a monotherapy or dual therapy or prevention regimen, treatment regimens may include triptans, ergotamines, nonsteroidal anti-inflammatory drugs (NSAIDs), nonnarcotic analgesics, blood pressure medications, anticonvulsants, antidepressants, serotonin antagonists, onabotulinum toxin, and caffeine, either alone or two such agents in combination. Medications used to prevent migraine attacks may generally include beta-blockers (e.g. propranolol, atenolol, metoprolol, nadolol, and timolol), calcium channel blockers (e.g. verapamil, diltiazem, nimodipine), tricyclic anti-depressants (e.g. amitriptyline, nortriptyline, imipramine), selective serotonin reuptake inhibitors (e.g. fluoxetine, paroxetine, and sertraline), anticonvulsants (e.g. divalproex sodium, gabapentin, and topiramate), serotonin antagonists (e.g. methysergide and methylergonovine), and other treatments that include magnesium salts (e.g. magnesium oxide, magnesium chloride slow release, and magnesium diglycinate), vitamins (e.g. riboflavin), and herbals (e.g. Mig-99 and petasites). Alternatively, the class of medications commonly used to prevent migraine attacks may be antibody or small molecule antagonists to CGRP. Such CGRP antagonists known to the skilled artisan include for example eptinesumab (ALD403), fremanezumab (TEV-48125), erenumab (AMG334), ubrogepant (MK-1602), MK-8031 (atogepant), olcegepant, or rimegepant (BHV-3000; BMS-927711) (See e.g. New strategies for the treatment and prevention of primary headache disorders, N. M. Schuster & A. M. Rapoport, Nature Reviews Neurology (2016) 12, 635-650).

As defined herein, therapy resistant migraine patients will include patients with "refractory migraine". As used herein refractory migraine includes but is not limited to refractory chronic migraine and/or refractory episodic migraine. Means of identification of refractory migraine patients are known to the skilled artisan. For example, refractory chronic migraine is recognized by the skilled artisan, as illustrated in the proposed criteria for this condition provided by the European Headache Federation (EHF) (See Headache Classification Committee of the International Headache Society (IHS). The International Classification of Headache Disorders, 3rd edition). The EHF recommends that refractory chronic migraine be defined as ICHD-3 beta chronic migraine without medication overuse in patients who have failed to respond to treatment with at least three preventive medications at adequate dosages, each with trials of at least 3 months. The proposed criteria can be briefly described as follows: A. ICHD-3 beta chronic migraine, with no medication overuse; B. prophylactic migraine medications in adequate dosages used for at least 3 months each; C. contraindications for or no effect of preventive medication with at least three drugs from the following classes: Beta blockers (Propranolol up to 240 mg daily, Metoprolol up to 200 mg daily, Atenolol up to 100 mg daily, Bisoprolol up to 10 mg daily), Anticonvulsants (Valproate acid up to 1.5 g daily, Topiramate up to 200 mg daily), Tricyclics (Amytriptyline up to 150 mg daily), or others (Flunarizine up to 10 mg daily, Candesartan up to 16 mg daily, OnabotulinumtoxinA 155-195 U according to the PREEMPT protocol), and D. Adequate treatment of psychiatric or other comorbidities by multidisciplinary team, if available.

An unsatisfactory treatment attempt is one in which the patient concludes after a full course of therapy that their symptoms were not alleviated to an extent such that disability was avoided. Preferably, the methods of the present invention provide prevention of migraine disability such that post a chronic nightly administration of lasmiditan regimen the migraine patient is free of significant clinical disability wherein the patient does not report migraine attacks and associated complete disability, or needing bed rest, or marked interference with daily activities. More preferably, the methods of the present invention prevent migraine disability such that post a chronic nightly administration of lasmiditan regimen the migraine patient is free of mild interference. More preferably the methods of the present invention prevent migraine disability such that post a chronic nightly administration of lasmiditan regimen the migraine patient is not at all disabled. Disability measures for migraine are well known to the skilled artisan, such as the Migraine Disability Assessment, where a total score $\geq 11$ may represent moderate-to-severe headache-related disability. In embodiments of the present invention a Migraine Disability Assessment of 10 or less, or an equivalent assessment by measures known to the skilled artisan, represents avoidance of disability. Preferably, the methods of the present invention prevent migraine disability such that patients report a total score on the Migraine Disability Assessment of 10 or less. Preferably, in embodiments of the present invention a Migraine Disability Assessment or an equivalent assessment by measures known to the skilled artisan will demonstrate no clinically disability.

Therapy resistant patients have yet to achieve substantial freedom from recurrent migraine, and thus represent a critical unmet need. Failure of these therapy resistant migraine patients to achieve adequate relief from multiple prior treatment regimens demonstrates that their disease is particularly difficult to treat, and efficacy in this population represents a surprising and superior outcome. The present invention arises from surprising and unexpected preclinical and clinical observations which provide evidence that lasmiditan has persistent and relatively long-lasting effects, effects which appear to endure after the compound is no longer present at levels for acute pharmacological action. Thus, these observations have led to the concept of chronic nightly dosing of lasmiditan for reduction in the susceptibility to migraine. The present methods provide a novel means to potentially modify the disease state of patients with recurrent migraine, and thereby reduce the patients' susceptibility to having recurrent migraines. These methods may be particularly useful in modifying the disease state of patients with recurrent migraine that have been refractory to two or more prior monotherapy and/or dual therapy treatment and/or prevention regimens, thus representing an important unmet medical need. More particularly, there exists an unmet need for alternative regimens to provide safe, tolerable, effective and convenient oral means to prevent migraines, and restore patients functioning to a relatively migraine disease-free state.

Novel methods are provided herein for the chronic nightly administration of lasmiditan to prevent migraine, and therapy resistant migraine. It is believed that the chronic nightly administration of lasmiditan will be superior to on-demand treatment and provide novel means to modify the disease state of patients with recurrent migraine, and thereby reduce the patients' susceptibility to having recurrent migraines. It is believed the pharmacological outcomes of these dosing regimens will result in superior efficacy for migraine prevention in patients who suffer from migraine, and prevent therapy resistant migraine which is defined herein as migraine refractory to two or more prior monotherapy and/or dual therapy migraine prevention regimens.

The methods of the present invention are believed to provide improved migraine prevention, including in patients who suffer from therapy resistant migraine wherein the patients migraines have been refractory to two or more prior monotherapy and/or dual therapy treatment regimens, and further provide a particularly advantageous combination of pharmacological benefits, comprising, safe, tolerable, and effective prevention of migraine attacks, and at the same time, provide a clinically tolerable level of adverse effects such as dizziness, paresthesia, and somnolence. The prevention methods of the present invention may provide these benefits in part by allowing the migraine patient to adequately prevent their migraine episodes with a lower dose of lasmiditan, for instance 25 mg, or 50 mg administered nightly, and alternatively, if the individual patient needs a higher dose, those patients can be administered 100 mg, 150 mg, or 200 mg, in order to achieve effective prevention. In this respect, the prevention methods of the present invention provide migraine patients with significant reduction, and/or more preferably with freedom from significant migraine symptoms and disability.

As used herein, "chronic nightly administration" includes the administration of lasmiditan as a specific treatment regimen intended to provide the beneficial effect from the long term and regular administration of lasmiditan at the specified doses. In particular, "chronic nightly administration" includes administration every night consecutively for not less than five nights in a row, or for as long as is needed to prevent the patients' migraine attacks. Further, "chronic nightly administration" includes administration every other night consecutively for not less than a period of ten nights total, or for as long as is needed to prevent the patients' migraine attacks. If a patient misses an occasional night, then the patient may simply resume administration on the next night specified for administration, and such an instance would continue to represent "chronic nightly administration". "Nightly" can include any particular time of day where the patient intends to sleep or rest for some period of hours as the patient would typically take as sleep time. "Nightly" can include any particular time of day "prior to sleep cycle", wherein "sleep cycle" is defined as the sleep portion of a 24 hour sleep/wake cycle, also known as a circadian rhythm. Preferably, "nightly administration" will occur 12 hours prior to the next window in which the patient desires to operate an automobile. Preferably, "nightly administration" will occur 8 hours prior to the next window in which the patient desires to operate an automobile. As used herein, "nightly" means lasmiditan is administered one time every 24-hour period, or one time every calendar day, preferably for not less than 5 consecutive days, or for as long as needed for migraine prevention. As used herein, a specified dose or dose range "nightly" or "per night" means that the dose or range is the maximum aggregate dose per night, or per the 24-hour period of a calendar day. As used herein, "chronic nightly" means lasmiditan is administered nightly, or every other night, on an ongoing consecutive basis, preferably for a period of not less than 10 days, or for as long as needed for migraine prevention. As used herein, "chronic" means lasmiditan is administered on an ongoing consecutive basis, where the patient administers the doses and/or wherein the patient is instructed to administer the doses as part of a treatment regimen.

As used herein, lasmiditan includes pharmaceutically acceptable salts thereof, including but not limited to 2,4,6-trifluoro-N-[6-(1-methyl-piperidin-4-ylcarbonyl)-pyridin-2-yl]-benzamide mono-hydrochloride salt, and 2,4,6-trifluoro-N-[6-(1-methyl-piperidine-4-carbonyl)-pyridin-2-yl]-benzamide hemi-succinate salt. Methods of preparing lasmiditan and salts and certain formulations and dosage forms thereof are known to the skilled artisan, and are described in WO 2003/084949 and/or WO 2011/123654.

Embodiments of the present invention contemplate combinations of lasmiditan with birth control agents for the prevention of menstrual migraine. Birth control agents are well known to the skilled artisan, such as combined oral contraceptive pill, also referred to as a birth control pill, which includes a combination of an estrogen (for instance ethinylestradiol) and a progestin.

In some embodiments, a patient is a human who has been diagnosed as having a condition or disorder in need of prevention with a pharmaceutical composition described herein. In some embodiments, a patient is a human that is characterized as being at risk of a condition or disorder for which administration with a pharmaceutical composition described herein is indicated. In those instances where the disorders which can be treated by the methods of the present invention are known by established and accepted classifications, such as migraine, episodic headache, chronic headache, chronic cluster headaches, and/or episodic cluster headaches, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress. Migraine patients can further be diagnosed with migraine, with or without aura (1.1 and 1.2), as defined by International Headache Society (IHS) International Classification of Headache Disorders, 3rd edition, (ICHD-3) beta version (The International Classification of Headache Disorders, 3rd edition (beta version), Cephalalgia 2013; 33: 629-808). In some embodiments, the human patient has been diagnosed with episodic migraine prior to receiving chronic administration of lasmiditan, preferably nightly, to prevent migraine. In some embodiments, the human patient has been diagnosed with chronic migraine prior to receiving lasmiditan. In some embodiments, the human patient experiences auras with their migraine headaches. In some embodiments, the human patient does not experience auras with their migraine headaches.

As used herein "migraine" includes but is not limited to migraine attacks. As used herein "migraine attack" refers to the following description. Symptoms may overlap within various phases of a migraine attack and not all patients experience the same clinical manifestations. In the prodrome phase, the majority of patients have premonitory symptoms that may precede the headache phase by up to 72 hours. These include changes in mood and activity, irritability, fatigue, food cravings, repetitive yawning, stiff neck, and phonophobia. These symptoms may endure well into the aura, headache, and even postdrome phases. Some patients experience an aura phase, wherein about one-third of patients experience transient neurological deficits during attacks. The ICHD-3 defines aura as 1 or more transient, fully reversible neurological deficits, of which at least 1 has to have a unilateral localization, that develops over 5 minutes or more, and of which each deficit lasts between 5 and 60 minutes. While a visual aura, which may show positive (fortification spectra), negative (scotoma), or both phenomena, is found in over 90% of the cases, and the most common deficit, sensory, motor, speech, brain stem, and retinal aura symptoms may also occur. A transient wave of neuronal depolarization of the cortex is believed to be the pathophysiological brain mechanism underlying the clinical phenomenon of migraine aura. In the headache phase, headache attacks which may last 4 to 72 hours are accompanied by nausea, photophobia and phonophobia, or both. The headache is characterized as unilateral, pulsating, of moderate or severe intensity, and aggravated by physical activity; two of these characteristics suffice to fulfill the diagnostic criteria. In the postdrome phase, characteristic symptoms reflect those observed during the premonitory phase. Typical postdrome symptoms include tiredness, difficulties in concentrating, and neck stiffness. It remains unclear whether these symptoms initiate in the premonitory phase and persist throughout the headache phase into the postdrome phase, if they may also initiate during the headache phase, or even appear after the headache phase has ended.

A "migraine headache" as used herein refers to headache, with or without aura, of ≥30 minutes duration, with both of the following required features (A and B): A) at least 2 of the following headache characteristics: 1) unilateral location, 2) pulsating quality, 3) moderate or severe pain intensity, and 4) aggravation by or causing avoidance of routine physical activity; AND B) during headache at least one of the following: a) nausea and/or vomiting, and/or b) photophobia and phonophobia. A "probable migraine headache" as used herein refers to a headache of greater than 30 minutes duration, with or without aura, but missing one of the migraine features in the International Headache Society ICHD-3 definition.

A "migraine headache day" as used herein refers to a calendar day on which a migraine headache or probable migraine headache occurs. An "ICHD migraine headache day" as used herein refers to a calendar day on which a migraine headache occurs. A "migraine headache attack" refers to the beginning on any day a migraine headache or probable migraine headache is recorded and ends when a migraine-free day occurs. A "non-migraine headache" refers to all headaches of greater than 30 minutes duration not fulfilling the definition of migraine or probable migraine. A "non-migraine headache day" refers to a calendar day on which a non-migraine headache occurs. A "headache day" refers to a calendar day on which any type of headache occurs (including migraine, probable migraine, and non-migraine headache).

"Episodic migraine" as used herein refers to 4 to 14 migraine headache days and <15 headache days per 30-day period in the prospective baseline period. "Chronic migraine" as used herein refers to at least 15 headache days per 30-day period in the prospective baseline period, of which at least 8 are migraine. A "migraine headache day" refers to a calendar day on which a migraine headache or probable migraine headache occurs.

The term "pharmaceutical" or "pharmaceutically acceptable" when used herein as an adjective, means substantially non-toxic and substantially non-deleterious to the recipient. By "pharmaceutical composition" it is further meant that the carrier, solvent, excipients and salt must be compatible with the active ingredient of the composition (e.g. a compound of the invention). It is understood by those of ordinary skill in this art that the terms "pharmaceutical formulation" and "pharmaceutical composition" are generally interchangeable, and they are so used for the purposes of this application. Additionally, the compounds of the present invention, for example, the salts of the compounds, can exist in either hydrated or unhydrated (the anhydrous) form. Nonlimiting examples of hydrates include monohydrates, dihydrates, etc. When the compounds of this invention are amines, they are basic in nature and accordingly react with any of a number of inorganic and organic acids to form pharmaceutically acceptable acid addition salts. The term "acid addition salt" refers to a salt of a compound prepared by reaction of the compound with a mineral or organic acid. The compounds of the present invention form pharmaceutically acceptable acid addition salts with a wide variety of organic and inorganic acids and include the physiologically acceptable salts which are often used in pharmaceutical chemistry. Such salts are also embodiments of this invention. A "pharmaceutically-acceptable (acid) addition salt" is formed from a pharmaceutically-acceptable acid as is well known in the art. Such salts include the pharmaceutically acceptable salts exemplified in Berge, S. M, Bighley, L. D., and Monkhouse, D. C., J. Pharm. Sci., 66:1, (1977), which are well known to those skilled in the art.

The term "effective amount" or "therapeutically effective amount" means an amount or dose of lasmiditan in a pharmaceutical composition, such as a total amount administered in an administration, which upon single or multiple dose administration to the patient, provides the desired pharmacological effect in the patient, for example an amount capable of activating 5-$HT_{1F}$ receptors. In a preferred embodiment, "effective amount" means an amount of lasmiditan that upon chronic nightly administration is capable of rendering a patient migraine attack free for one or more days following administration. A "dose" refers to a predetermined quantity of lasmiditan calculated to produce the desired therapeutic effect in a patient. As used herein "mg" refers to milligram. As used herein, doses described in mg, refer to the active pharmaceutical ingredient lasmiditan as free-base equivalent by mass, for instance a "100 mg" dose, refers to 100 mg of the active pharmaceutical ingredient lasmiditan as free-base equivalent. As used herein, a given dose may be interpreted to describe doses of about the indicated amount, in that doses which are up to 10 percent higher or lower than the indicated dose are likewise contemplated to provide useful regimens in a manner similar to the indicated dose.

As used herein, the term "prevention" (or "prevent" or "preventing") refers to precluding, averting, obviating, forestalling, reducing the incidence of, stopping, or hindering the symptoms of a disease, disorder and/or condition. Prevention refers to administration of an agent to a subject who does not exhibit symptoms of a disease, disorder, and/or condition at the time of administration. In contrast the term "treating" or "treatment", as used herein, means to mitigate or modulate an already present disease state or condition, e.g., an existing migraine attack in a patient or subject. In embodiments that refer to a method of prevention as described herein, such embodiments are also further embodiments for use in that prevention, or alternatively for the manufacture of a medicament for use in that prevention.

As used herein, the term "reduction in the susceptibility to migraine" refers to a change in the disease state of a migraine patient wherein the etiopathological factors, and/or organ dysfunction, as for example in the trigeminal nervous system, which predispose the patient to susceptibility to migraine, have now been modified such that, with respect to migraine, the patient has become closer to homeostasis and the propensity and/or risk of that patient having a subsequent migraine has been significantly clinically decreased. A "reduction in the susceptibility to migraine" can be observed in a migraine patient, wherein the patient has fewer migraine headache days, and/or fewer migraine attacks, following treatment with chronic administration of lasmiditan, even though the blood and or tissue levels of lasmiditan sufficiently low and or absent such that the prior administered doses are no longer engaging with 5-$HT_{1F}$ receptors in the known pharmacologically meaningful dose response range. That is, the prior chronic nightly administration of lasmiditan is no longer present, but has resulted in disease modification in the patient. That disease modification being a subsequent reduction in the susceptibility to migraine. This reduction in the susceptibility to migraine leaves the patient closer to the state of being clinically free of migraine attacks, and thus manifests in greatly reduced migraine induced disability, and promotes resumption of normal daily life activities.

As used herein, the terms "month," "monthly," and derivations thereof, refer to a time period that is from 28 to 31 consecutive days unless otherwise stated. The term "about" as used herein, means in reasonable vicinity of the stated numerical value, such as plus or minus 10% of the stated numerical value.

Non-limiting examples of propranolol include propranolol hydrochloride, ANAPRILIN®, AVLOCARDYL®, INDERAL®, OBZIDAN®, REXIGEN®, BETADREN®, DEXPROPRANOLOL®, and DOCITON®. Non-limiting examples of metoprolol include metoprolol fumarate, metoprolol succinate, metoprolol tartrate, LOPRESSOR®, BETALOC®, TORPOL®, SELOKEN®, SPESIKOR®, SPESICOR®, and TOPROL XL®. Non-limiting examples of topiramate include topiramate calcium, topiramate potassium, topiramate sodium, and TOPAMAX®. Non-limiting examples of valproate include valproate sodium, divalproex sodium, divalproex, valproic acid, DEPACON®, DEPAKENE®, and DEPAKOTE®. Non-limiting examples of amitriptyline include amitriptyline hydrochloride, amitriptyline pamoate, ELAVIL®, and LEVATE®. Non-limiting examples of flunarizine include flunarizine dihydrochloride, flunarizine hydrochloride, SIBELIUM®, FLUFENAL®, FLUVERT®, ZINASEN®, ISSIUM®, VERTIX®, NOVO-FLUNARIZINE®, and APO-FLUNARIZINE®. Non-limiting examples of candesartan include candesartan cilexetil, BIOPRESS®, ATACAND®, AMIAS®, and RATACAND®. Non-limiting examples of botulinum toxin A include onabotulinumtoxinA, BOTOX®, DYSPORT®, and XEOMIN®. Non-limiting examples of botulinum toxin B include rimabotulinumtoxinB and MYOBLOC®.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, L. V. Allen, Editor, 22nd Edition, Pharmaceutical Press, 2012). In particular, the components of the present combinations may be combined in the same formulation where appropriate, or alternatively they can be formulated separately.

In a formulation lasmiditan is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

Lasmiditan or vehicle is administered via oral gavage one hour prior to electrical stimulation of the trigeminal ganglion. Lasmiditan doses are reported as free base-equivalents. Data are expressed as the extravasation ratio (stimulated/unstimulated). Data are represented as mean±SEM. *$p<0.05$ vs vehicle (ANOVA followed by Dunnett's post-hoc, mean±SEM, n=4).

Figure 2:
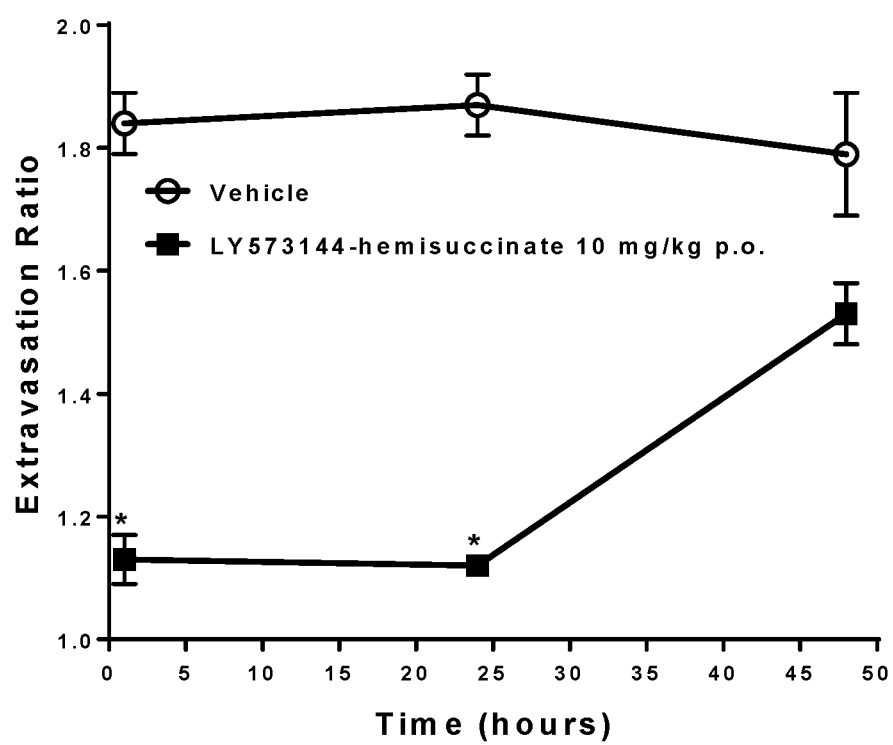

FIG. 2: Inhibition of trigeminal stimulation-induced plasma protein extravasation in the dura of rats following pretreatment with 2,4,6-trifluorotrifluoro-N-[6-(1-methyl-piperidine-4-carbonyl)-pyridin-2-yl]-benzamide hemi-succinate salt (10 mg/kg, po) or vehicle ($H_2O$).

Lasmiditan or vehicle is administered via oral gavage either 1, 24 or 48 hours prior to electrical stimulation of the trigeminal ganglion. Lasmiditan dose is reported as free base-equivalents. Data are expressed as the extravasation ratio (stimulated/unstimulated). Data are represented as mean±SEM. *$p<0.05$ vs vehicle (ANOVA followed by Dunnett's post-hoc, mean±SEM, n=4).

Figure 3:
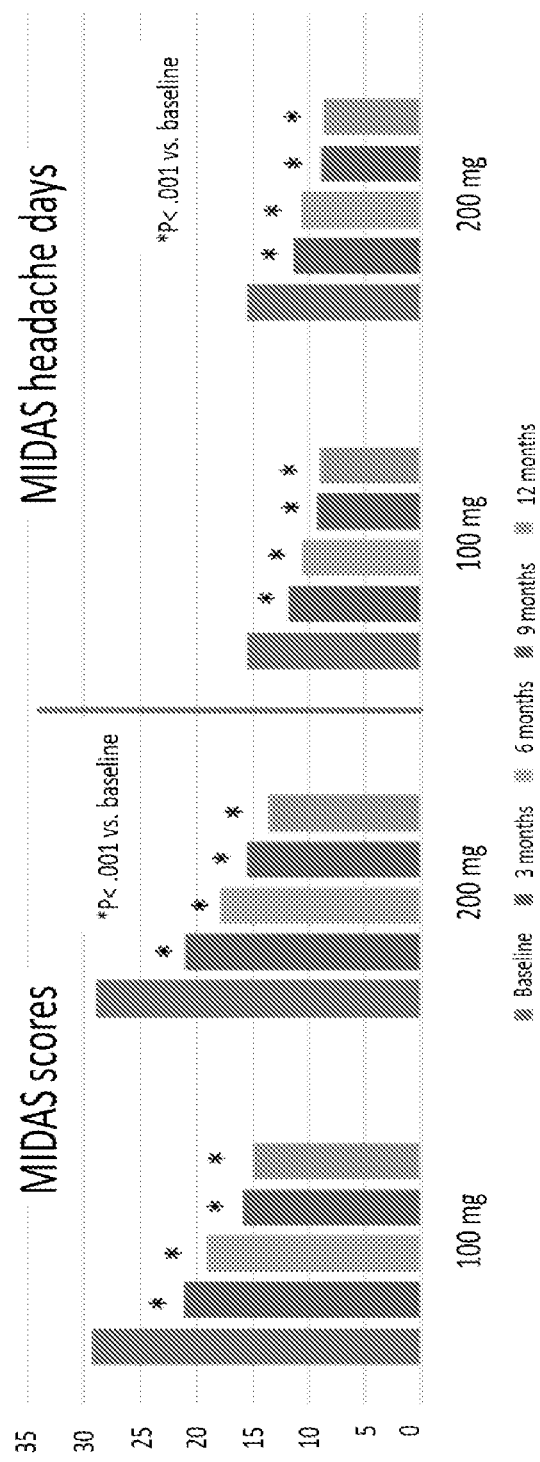

FIG. 3. Disability improvements over 12 months with lasmiditan for acute treatment of migraine: interim analysis of Migraine Disability Assessment (MIDAS) scale changes in the GLADIATOR study.

Figure 4:
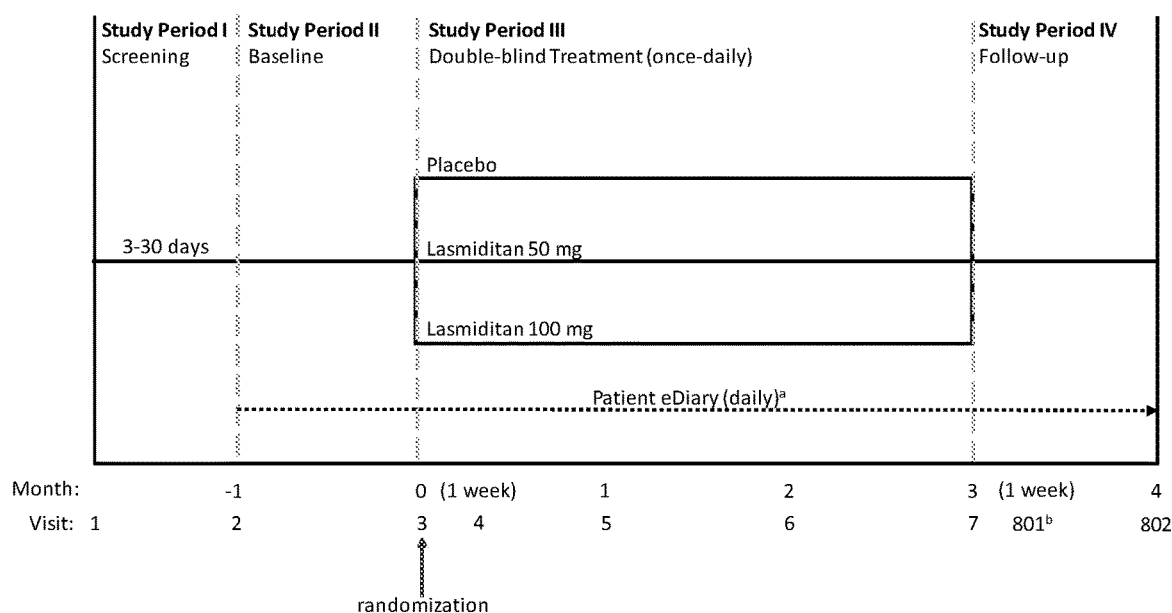

FIG. 4: Schema for Study LAIL, a Phase 2, multicenter, double-blind, randomized, placebo-controlled study of lasmiditan in adult patients with episodic migraine.

EXAMPLES

Example 1: Pre-Clinical Studies of Neurogenic Inflammation of the Dural Membrane, and Activation of the Trigeminal Nervous System Migraine is a painful condition thought to involve neurogenic inflammation of the dural membrane and activation of the trigeminal nervous system. The $5-HT_{1F}$ receptor is widely expressed in the CNS and peripheral nerves, including the trigeminal ganglia, dorsal root ganglia and trigeminal nucleus caudalis. Plasma protein extravasation (PPE), one component of neurogenic inflammation, can be induced in the dura of rats by electrically stimulating the trigeminal ganglion. Considering the role of the trigeminal nerve in the physiology of migraine, this study is useful to characterize the ability of lasmiditan-hemisuccinate to block plasma protein extravasation in the dura of rats following electrical stimulation of the trigeminal ganglion.

To investigate the potential of lasmiditan to modify the dysfunction in the target tissue, the duration of effect following a single oral dose of lasmiditan-hemisuccinate was also determined. Electrical stimulation of the trigeminal ganglion of rats and guinea pigs can be used to induce neurogenic inflammation in the meninges (dura). Briefly, unilateral electrical stimulation of either the left or right trigeminal ganglion using electrodes implanted stereotaxically is used to induce ipsilateral neurogenic inflammation and the increased extravasation of plasma proteins.

The selective $5-HT_{1F}$ agonist lasmiditan (lasmiditan-hemisuccinate) is shown to inhibit dural plasma protein extravasation in Sprague Dawley rats following oral (po) dosing. Lasmiditan-hemisuccinate significantly blocks dural PPE 24 hours following oral administration of a single 10 mg/kg dose. However, the compound was not effective 48 hours post-dose. The concentration of lasmiditan in plasma and brain is measured for all dose levels and time points at the termination of each experiment.

The efficacy observed 24 hours post-dose is not explained by lasmiditan exposure in either compartment, thus surprisingly and unexpectedly represents a protracted pharmacological effect, that is one which is believed to reflect a potential modification in migraine disease susceptibility. Thus, the present invention, which provides dosing and dosing regimens for the use of lasmiditan for the modification of migraine disease susceptibility, is supported by this unexpected in-vivo observation in a model of neurogenic inflammation of the dural membrane, and activation of the trigeminal nervous system.

Evaluation of Compound Potency 1 Hour Following Oral Administration

Lasmiditan-hemisuccinate is dissolved in sterile water. All doses of lasmiditan are reported as free base equivalent doses, accounting for the weight of the salt. Envigo Sprague-Dawley, Sprague-Dawley male rats (250-350 grams, n=4/group) are fasted overnight prior to dosing. The animals are orally gavaged (2 mL/kg dose volume) with test compound or vehicle one hour prior to stimulation time and returned to their cages with only water available. Approximately 50 minutes post-dosing, the rats are anesthetized with Nembutal (65 mg/kg, ip.) and implanted with stainless steel stimulating electrodes (Rhodes Medical Systems, Inc.) to a depth of 9.2 mm. from the dura. The femoral vein is exposed and fluorescein isothiocyanate-labeled bovine serum albumin (FITC-BSA) (20 mg/kg, iv.), is injected into the femoral vein 2 minutes prior to stimulation. The FITC-BSA functions as a marker for protein extravasation. The left trigeminal ganglion is stimulated for 5 minutes at a current intensity of 1.0 mA (5 Hz, 5 msec pulse duration) with a Model S48 Grass Instrument Stimulator with PSIU6 photoelectric isolation unit (Grass-Telefactor). Five minutes following stimulation, a blood sample is collected by cardiac puncture and the rats are sacrificed by exsanguination with 40 ml of saline. One milliliter of blood is collected and placed in a 1.5 ml EDTA coated tube (Fisher Cat. #540734) on ice. Plasma is separated via centrifugation at 10,000 rpm (941 g) for thirty minutes at 4° C. The top of the skull is removed to collect the brain and dural membranes. The brain and plasma samples are frozen at −80° C. until thawed for compound quantification. The membrane samples are removed from both hemispheres, rinsed with water, and spread flat on microscope slides. The slides are dried for 15 minutes on a slide warmer, then the tissues are cover-slipped with a 70% glycerol/water solution. A fluorescence microscope (Zeiss) equipped with a grating monochromator and a spectrophotometer is used to quantify the amount of FITC-BSA dye in each dural sample. The extravasation induced by electrical stimulation of the trigeminal ganglion is an ipsilateral effect (i.e. occurs only on the side of the dura in which the trigeminal ganglion was stimulated). This allows the other (unstimulated) half of the dura to be used as the control. The ratio of extravasation in the dura from the stimulated side versus the unstimulated side is calculated and reported as the extravasation ratio for each animal. The mean extravasation ratio and standard error of the mean (SEM) are calculated for each treatment group. Controls yield a ratio of approximately 1.8. In contrast, a compound which effectively prevents the extravasation in the dura from the stimulated side would have a ratio of approximately 1. The resulting data are analyzed with a one-way ANOVA followed by Dunnett's post hoc to determine statistical significance (p<0.05). Levels of compound in the plasma and brain samples for each animal are analyzed according to methods known to the skilled artisan.

Evaluation of Compound Potency 24 or 48 Hours Following Oral Administration

Envigo Sprague-Dawley, Sprague-Dawley male rats (250-350 grams, n=4/group) are fasted overnight prior to dosing for the duration p.o. study. The animals are orally gavaged with test compound or vehicle and returned to their cages with only water available; with food returned 1 hour later. Either 24 or 48 post-dose, the animals are anesthetized with Nembutal (65 mg/kg, ip.) and placed in a stereotaxic frame (David Kopf Instruments). The remainder of the protocol is identical to the method immediately above for Evaluation of Compound Potency 1 Hour Following Oral Administration.

Figure 1:
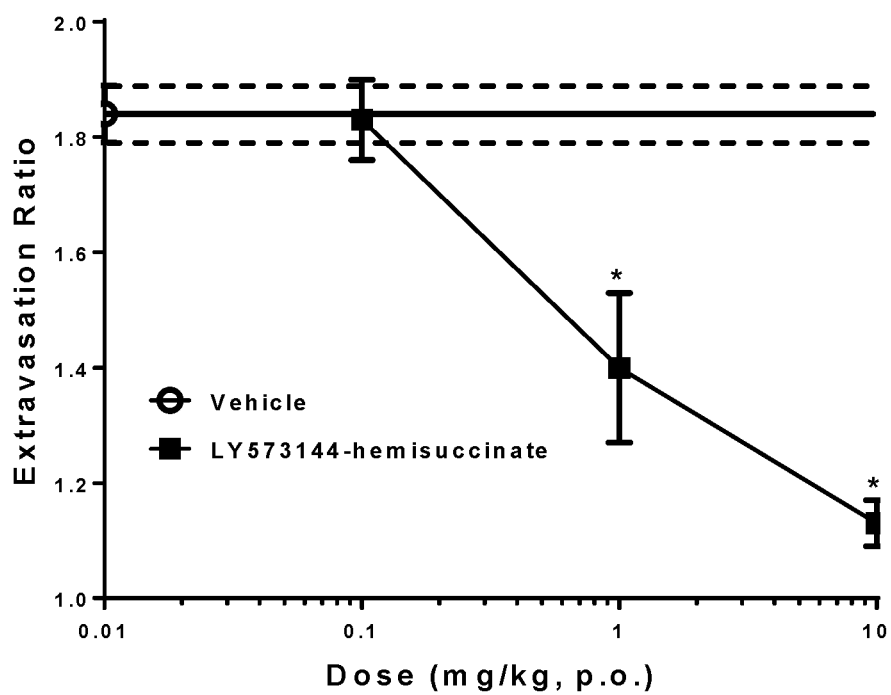
FIG. 1: Inhibition of trigeminal stimulation-induced plasma protein extravasation in the dura of rats following pretreatment with 2,4,6-trifluorotrifluoro-N-[6-(1-methyl-piperidine-4-carbonyl)-pyridin-2-yl]-benzamide hemi-succinate salt or vehicle ($H_2O$).

Results:

Lasmiditan-hemisuccinate dose-dependently inhibits dural plasma protein extravasation when evaluated one hour following oral administration to rats. Doses of 1 and 10 mg/kg, but not 0.1 mg/kg, are statistically different vs vehicle treated animals (FIG. 1). In order to assess the pharmacological duration of effect, inhibition of dural plasma protein extravasation is evaluated 1, 24 and 48 hours after a single oral (10 mg/kg) dose of lasmiditan. Surprisingly, this dose of lasmiditan is equally efficacious 1 and 24 hours post-dose, but not at 48 hours (FIG. 2). Unbound plasma and brain levels of lasmiditan, measured one hour post-administration, increased with dose as shown in Table 1. However, the unbound plasma and brain concentrations measured 24 hours following the administration of the 10 mg/kg dose, are not different from the exposures associated with the non-efficacious 0.1 mg/kg dose at one hour. As such, the efficacy of lasmiditan observed 24 hours post-dose is not due to a long compound exposure profile.

TABLE 1

Unbound plasma and brain levels of lasmiditan in rats from dural plasma protein extravasation studies

| Dose (mg/kg, po) | Time post-dose (hrs) | Unbound Plasma Conc (nM, mean ± SD; n = 4) | Unbound Brain Conc (nM, mean ± SD; n = 4) |
| --- | --- | --- | --- |
| 0.1 | 1  | 6.0 ± 1.9   | 2.0 ± 0.1  |
| 1   | 1  | 67 ± 19.8   | 16.6 ± 3.6 |
| 10  | 1  | 767 ± 254   | 242 ± 95   |
| 10  | 24 | 6.2 ± 2.5   | 2.1 ± 0.9  |
| 10  | 48 | BQL         | BQL        |

$FU_{plasma} = 0.459$,
$FU_{brain} = 0.117$,
BQL - below quantitation level

Example Clinical Studies

Lasmiditan has been shown to be effective for the acute on demand treatment of migraine with or without aura in adults. In Phase 3 trials, lasmiditan showed statistically significant superiority over placebo on the primary endpoint of pain freedom and the key secondary endpoint of MBS freedom at 2 hours after taking study drug. Lasmiditan was generally well tolerated with the most common TEAEs including dizziness, paresthesia, somnolence, fatigue, and nausea. Generally, these TEAEs were mild or moderate in severity and short in duration. All doses of lasmiditan were associated with driving impairment in a study of healthy volunteers on a computer-based driving simulator. Patients should restrict their driving, operation of heavy machinery, or other similar activities after taking study drug as described in the informed consent form (ICF). Clinical data from the acute treatment program suggest that single and multiple doses of intermittently administered lasmiditan may have preventive effects on migraine. A concept of the present invention is that consistent once-nightly administration of lasmiditan may decrease the frequency of migraine attacks.

The following clinical study designs further illustrate the invention, but should not be construed to limit the scope of the invention in any way. Below are provided examples of studies of lasmiditan in the prevention of migraine. It will be understood by the skilled artisan that similar studies can be conducted with patients who have been unable to successfully manage their migraine attacks with either lasmiditan or galcanezumab individually. It will be understood by the skilled artisan that similar studies can be conducted with patients, referred to herein as therapy resistant migraine patients, who have migraine attacks which are refractory to two or more prior monotherapy and/or dual therapy treatment and/or prevention regimens. The skilled artisan can conduct similar studies with patients suffering from a headache selected from the group consisting of episodic headache, chronic headache, chronic cluster headache, or episodic cluster headache, including patients with therapy resistant headaches. The skilled artisan may readily identify, using methods described herein and methods known in the art, patients who have been unable to successfully manage their migraine attacks with either lasmiditan or galcanezumab individually, and/or therapy resistant migraine patients, who have migraine attacks which are refractory to two or more prior monotherapy and/or dual therapy treatment and/or prevention regimens, wherein said patients so identified may be subjects for clinical studies such as those described herein.

Methods of conducting such clinical trials are known to the skilled artisan and illustrated for instance by the citations for published lasmiditan clinical studies provided herein. Methods to assess migraine treatments include Patient Reported Outcomes (PRO) such as Quality of Life (QOL) Measures, including for example: Migraine-Specific Quality of Life, version 2.1 (MSQ v2.1), Headache Impact Test-6 (HIT-6), Migraine Disability Assessment Scale (MIDAS), Migraine Specific Quality of Life Questionnaire (MSQoL). In addition, an ePRO daily diary can be used to record headache and other migraine symptoms. Based on the diary data, using an automated algorithm, the days can be categorized as Migraine Headache Days (MHDs) (including probable MHD). A probable migraine is defined as a headache with or without aura and lasting ≥30 minutes but missing one of the migraine features in the ICHD-3 beta criteria. The monthly number of MHDs with acute migraine medication use can be obtained through the ePRO diary, and the PGI-S, MSQ, and MIDAS assessments are performed at the study site at every monthly visit for PGI-S and MSQ and on months 3 and 6 for MIDAS with the use of a slate device. A study design can be formulated to compare the efficacy of each nightly dosing regimen compared with placebo, on the overall mean change from baseline in the number of monthly migraine headache days (MHDs) during the treatment phase, based on the ePRO or other relevant clinical data. Other possible outcome measures can be the mean proportion of patients with reduction from baseline in monthly MHDs during the double-blind treatment phase, the mean change from baseline in the Role Function-Restrictive (R-FR) domain score of the Migraine-Specific Quality of Life Questionnaire version 2.1 (MSQ v2.1), the mean change from baseline in the Patient Global Impression of Severity (PGI-S) rating (average of selected months), and/or an outcome measure for the Migraine Disability Assessment (MIDAS) total score. These and other migraine treatment assessments are well known to the skilled artisan.

Example 2: Disability Improvements Over 12 Months with Lasmiditan for Acute Treatment of Migraine: Interim Analysis of Migraine Disability Assessment (MIDAS) Scale Changes in the GLADIATOR Study The placebo-controlled Phase 3 studies SAMURAI (NCT02439320) and SPARTAN (NCT02605174) evaluated lasmiditan 50 mg [SPARTAN only], 100 mg and 200 mg. In comparison with placebo, all doses of lasmiditan showed significantly higher rates of freedom from pain and freedom from most bothersome symptoms two hours post dose (Kuca et al. J Head and Face Pain 2017; 57:1311-2, Wietecha et al. Cephalgia 2017; 37(suppl):367-8). GLADIATOR (NCT02565186) is a prospective randomized open-label Phase 3 study to evaluate long-term intermittent use of lasmiditan (100 mg or 200 mg) for acute treatment of migraine. An interim analysis of the effects of lasmiditan on migraine disability assessed with the MIDAS scale in GLADIATOR is described below, and has provided surprising and unexpected evidence of persistent beneficial effects in migraine patients.

Methods:

Patients who completed SAMURAI or SPARTAN were offered participation in GLADIATOR with randomization to lasmiditan 100 mg or lasmiditan 200 mg which represents an uncontrolled, open-label study. Patients were randomized to either lasmiditan 100 mg or lasmiditan 200 mg regardless of their treatment assignment in the feeder studies, and did not necessarily use lasmiditan for all their migraine attacks. This interim analysis includes patients with MIDAS score data at baseline of GLADIATOR and post-baseline assessments. The analysis presented is based on the MIDAS questionnaire administered at baseline and at months 3, 6, 9 and 12. An additional analysis was also conducted in the subgroup of patients who completed 12 months. Changes were modelled using a mixed model repeated measures analysis MIDAS measures lost time due to migraine in days over 3 months. Domains included are activity limitations at work, household work or family, social and leisure activity. MIDAS has demonstrated reliability and validity; scores correlate with clinical judgement on the need for medical care (See Stewart et al. Neurology 1999; 53:988-94, and Stewart et al. Neurology 2001; 56: S20-8).

Overview of GLADIATOR Study Design:

Key inclusion criteria were patients who were eligible for SAMURAI or SPARTAN and had at least moderate migraine disability (MIDAS score ≥11). Patients were randomized 1:1 for acute treatment of migraine with either lasmiditan 100 mg for up to 12 months, or lasmiditan 200 mg for up to 12 months. Patients used lasmiditan as the first treatment for each new migraine attack (≤4 hours of Migraine pain onset). A second dose was permitted between 2 and 24 hours for rescue (Rescue: did not achieve headache pain-free status at 2 hours, completed the 2-hour assessments and took a second dose of study drug between 2 and 24 hours post-first dose) or recurrence (Recurrence: achieved headache pain-free status at 2 hours, but then experienced recurrence of mild, moderate or severe migraine pain and took a second dose of study drug up to 24 hours from the first dose) of migraine. Assessments of safety and efficacy were conducted, including MIDAS questionnaires at baseline and months 3, 6, 9 and 12.

MIDAS Questionnaire (See for example Stewart et al., Neurology 1999; 53:988-94, Stewart et al., Neurology 2001; 56: S20-8) The sum of Questions 1-5 below represents the Total MIDAS score.

1. On how many days in the past 3 months did you miss work or school because of your headaches?
2. How many days in the past 3 months was your productivity at work or school reduced by half or more because of your headaches? (Do not include days you counted in question 1 where you missed work or school)
3. On how many days in the past 3 months did you not do household work (such as housework, home repairs and maintenance, shopping, caring for children and relatives) because of your headaches?
4. How many days in the past 3 months was your productivity in household work reduced by half of more because of your headaches? (Do not include days you counted in question 3 where you did not do household work)
5. On how many days in the past 3 months did you miss family, social or leisure activities because of your headaches?

Additional questions include:

A. On how many days in the past 3 months did you have a headache? (If a headache lasted more than 1 day, count each day)
B. On a scale of 0-10, on average how painful were these headaches? (where 0=no pain at all, and 10=pain as bad as it can be)

Results:

A summary of baseline characteristics is provided in Table 2. Data are presented on a total of 2037 patients treated for an average of 5.6 months. The mean age is 43.2 years and the sample includes 85% women.

TABLE 2

| Treatment group | Lasmiditan 100 mg (N = 974) | Lasmiditan 200 mg (N = 1063) |
|---|---|---|
| Age, mean years (SD) | 42.8 (12.3) | 43.6 (12.4) |
| Female, n (%) | 828 (85.0) | 904 (85.0) |
| Body mass index, kg/m$^2$ | 31.1 (8.2) | 31.0 (8.1) |
| White, n (%) | 774 (76.4) | 837 (78.7) |
| History of migraine, mean years (SD) | 18.8 (12.8) | 18.8 (12.9) |
| Migraine attacks/month, mean n (SD)† | 5.2 (1.8) | 5.2 (1.8) |
| Migraine with aura, n (%) | 356 (36.6) | 366 (34.5) |
| Migraine preventative medication use, n (%) | 214 (22.0) | 234 (22.0) |
| MIDAS total score, mean (IQR) | 29.4 (15, 36) | 28.9 (15, 35) |
| Headache past 3 months, mean days (IQR) | 15.5 (8, 20) | 15.5 (8, 20) |

TABLE 2-continued

| Treatment group | Lasmiditan 100 mg (N = 974) | Lasmiditan 200 mg (N = 1063) |
|---|---|---|
| Severity of headache pain, mean (IQR) Scale 0 (no pain) to 10 (bad as it can be) | 7.4 (7, 8) | 7.3 (6, 8) |

†Past 3 months,
MIDAS is Migraine Disability Assessment,
SD is Standard Deviation.

IQR is interquartile range.
Grade definitions for the MIDAS scores are shown in the table below.

| MIDAS Score | Grade definition |
|---|---|
| 0-5 | Little or no disability |
| 6-10 | Mild disability |
| 11-20 | Moderate disability |
| 21+ | Severe disability |

TABLE 3

GLADIATOR: MIDAS total scores

| Group | Mean Midas Total Score [IQR] | Subjects |
|---|---|---|
| Baseline | 29.4 [15, 36] | n = 972 |
| Lasmiditan 100 mg 3 Months | 21.2 [10, 26]* | n = 818 |
| Lasmiditan 100 mg 6 Months | 19.1 [8, 24.5]* | n = 672 |
| Lasmiditan 100 mg 9 Months | 17.3 [7, 21]* | n = 541 |
| Lasmiditan 100 mg 12 Months | 15.3 [5, 20]* | n = 429 |

*P <0.001 vs. baseline; mixed model for repeated measures.

There were no significant differences between the lasmiditan doses.

TABLE 4

GLADIATOR: MIDAS total scores

| Group | Mean Midas Total Score [IQR] | Subjects |
|---|---|---|
| Baseline | 28.9 [15, 35] | n = 1063 |
| Lasmiditan 200 mg 3 Months | 21.1 [9, 25]* | n = 884 |
| Lasmiditan 200 mg 6 Months | 18.1 [7, 22]* | n = 719 |
| Lasmiditan 200 mg 9 Months | 16.1 [5, 19]* | n = 581 |
| Lasmiditan 200 mg 12 Months | 13.4 [4, 16]* | n = 418 |

*P <0.001 vs. baseline; mixed model for repeated measures.

There were no significant differences between the lasmiditan doses

TABLE 5

GLADIATOR: MIDAS total scores for patients with data at 12 months (completers analysis)

| Group | Mean Midas Total Score [IQR] | Subjects |
|---|---|---|
| Baseline | 27.7 [15, 34] | n = 429 |
| Lasmiditan 100 mg 3 Months | 20.5 [10, 24.5]* | n = 428 |
| Lasmiditan 100 mg 6 Months | 18.2 [8, 24]* | n = 428 |
| Lasmiditan 100 mg 9 Months | 16.7 [7, 21]* | n = 429 |
| Lasmiditan 100 mg 12 Months | 15.3 [5, 20]* | n = 429 |

*P <0.001 vs. baseline; mixed model for repeated measures.

There were no significant differences between the lasmiditan doses.

TABLE 6

GLADIATOR: MIDAS total scores for patients with data at 12 months (completers analysis)

| Group | Mean Midas Total Score [IQR] | Subjects |
|---|---|---|
| Baseline | 26.2 [14, 31] | n = 418 |
| Lasmiditan 200 mg 3 Months | 18.6 [9, 22]* | n = 418 |
| Lasmiditan 200 mg 6 Months | 16.3 [6, 20]* | n = 416 |
| Lasmiditan 200 mg 9 Months | 15.3 [5, 17]* | n = 418 |
| Lasmiditan 200 mg 12 Months | 13.4 [4, 16]* | n = 418 |

*P <0.001 vs. baseline; mixed model for repeated measures.

There were no significant differences between the lasmiditan doses.

TABLE 7

GLADIATOR: MIDAS headache days in past 3 months

| Group | Mean days with headache in past 3 months [IQR] | Subjects |
|---|---|---|
| Baseline | 15.5 [8, 20] | n = 974 |
| Lasmiditan 100 mg 3 Months | 11.8 [4.5, 15]* | n = 820 |
| Lasmiditan 100 mg 6 Months | 10.6 [4, 14]* | n = 673 |
| Lasmiditan 100 mg 9 Months | 9.5 [3, 13]* | n = 541 |
| Lasmiditan 100 mg 12 Months | 8.8 [3, 10]* | n = 429 |

*P <0.001 vs. baseline; mixed model for repeated measures.

There were no significant differences between the lasmiditan doses.

TABLE 8

GLADIATOR: MIDAS headache days in past 3 months

| Group | Mean days with headache in past 3 months [IQR] | Subjects |
|---|---|---|
| Baseline | 15.5 [8, 20] | n = 1063 |
| Lasmiditan 200 mg 3 Months | 11.3 [4, 15]* | n = 884 |

TABLE 8-continued

GLADIATOR: MIDAS headache days in past 3 months

| Group | Mean days with headache in past 3 months [IQR] | Subjects |
|---|---|---|
| Lasmiditan 200 mg 6 Months | 10.9 [4, 14]* | n = 719 |
| Lasmiditan 200 mg 9 Months | 9.0 [3, 12]* | n = 582 |
| Lasmiditan 200 mg 12 Months | 8.2 [2, 10]* | n = 418 |

*P <0.001 vs. baseline; mixed model for repeated measures.

There were no significant differences between the lasmiditan doses.

TABLE 9

GLADIATOR: MIDAS headache days in past 3 months for patients with data at 12 months (completers analysis)

| Group | Mean days with headache in past 3 months [IQR] | Subjects |
|---|---|---|
| Baseline | 14.3 [8, 18] | n = 429 |
| Lasmiditan 100 mg 3 Months | 10.6 [5, 15]* | n = 428 |
| Lasmiditan 100 mg 6 Months | 10.2 [4, 13]* | n = 428 |
| Lasmiditan 100 mg 9 Months | 9.2 [3, 12]* | n = 429 |
| Lasmiditan 100 mg 12 Months | 8.8 [3, 10]* | n = 429 |

*P <0.001 vs. baseline; mixed model for repeated measures.

There were no significant differences between the lasmiditan doses.

TABLE 10

GLADIATOR: MIDAS headache days in past 3 months for patients with data at 12 months (completers analysis)

| Group | Mean days with headache in past 3 months [IQR] | Subjects |
|---|---|---|
| Baseline | 14.5 [7, 18] | n = 418 |
| Lasmiditan 200 mg 3 Months | 10.6 [4, 15]* | n = 418 |
| Lasmiditan 200 mg 6 Months | 10.0 [4, 12.5]* | n = 416 |
| Lasmiditan 200 mg 9 Months | 8.5 [3, 12]* | n = 418 |
| Lasmiditan 200 mg 12 Months | 8.2 [2, 10]* | n = 418 |

*P <0.001 vs. baseline; mixed model for repeated measures.

There were no significant differences between the lasmiditan doses.

TABLE 11

GLADIATOR: MIDAS headache pain in past 3 months

| Group | Mean headache pain in past 3 months [IQR] † | Subjects |
|---|---|---|
| Baseline | 7.4 [7, 8] | n = 974 |
| Lasmiditan 100 mg 3 Months | 7.0 [6, 8]* | n = 820 |
| Lasmiditan 100 mg 6 Months | 6.7 [6, 8]* | n = 673 |
| Lasmiditan 100 mg 9 Months | 6.7 [6, 8]* | n = 541 |
| Lasmiditan 100 mg 12 Months | 6.4 [5, 8]* | n = 429 |

*P <0.001 vs. baseline; mixed model for repeated measures.
† Scored 0-10, where 0 = no pain at all, and 10 = pain as bad as it can be.

There were no significant differences between the lasmiditan doses.

TABLE 12

GLADIATOR: MIDAS headache pain in past 3 months

| Group | Mean headache paint in past 3 months [IQR] † | Subjects |
|---|---|---|
| Baseline | 7.3 [6, 8] | n = 1063 |
| Lasmiditan 200 mg 3 Months | 6.9 [6, 8]* | n = 884 |
| Lasmiditan 200 mg 6 Months | 6.7 [6, 8]* | n = 718 |
| Lasmiditan 200 mg 9 Months | 6.5 [6, 8]* | n = 580 |
| Lasmiditan 200 mg 12 Months | 6.2 [5, 8]* | n = 415 |

*P <0.001 vs. baseline; mixed model for repeated measures.
† Scored 0-10, where 0 = no pain at all, and 10 = pain as bad as it can be.

There were no significant differences between the lasmiditan doses.

TABLE 13

GLADIATOR: MIDAS headache pain in past 3 months for patients with data at 12 months (completers analysis)

| Group | Mean headache pain in past 3 months [IQR] † | Subjects |
|---|---|---|
| Baseline | 7.4 [7, 8] | n = 429 |
| Lasmiditan 100 mg 3 Months | 7.1 [6, 8] ¶ | n = 428 |
| Lasmiditan 100 mg 6 Months | 6.9 [6, 8]* | n = 428 |
| Lasmiditan 100 mg 9 Months | 6.8 [6, 8]* | n = 429 |
| Lasmiditan 100 mg 12 Months | 6.4 [5, 8]* | n = 429 |

*P <0.001,
¶ P = 0.003 vs. baseline; mixed model for repeated measures.
† Scored 0-10, where 0 = no pain at all, and 10 = pain as bad as it can be.
There were no significant differences between the lasmiditan doses.

TABLE 14

GLADIATOR: MIDAS headache pain in past 3 months for patients with data at 12 months (completers analysis)

| Group | Mean headache pain in past 3 months [IQR] † | Subjects |
|---|---|---|
| Baseline | 7.4 [7, 8] | n = 415 |
| Lasmiditan 200 mg 3 Months | 7.0 [6, 8]* | n = 415 |
| Lasmiditan 200 mg 6 Months | 6.8 [6, 8]* | n = 413 |

TABLE 14-continued

GLADIATOR: MIDAS headache pain in past 3 months for
patients with data at 12 months (completers analysis)

| Group | Mean headache pain in past 3 months [IQR] † | Subjects |
|---|---|---|
| Lasmiditan 200 mg 9 Months | 6.5 [6, 8]* | n = 415 |
| Lasmiditan 200 mg 12 Months | 6.2 [5, 8]* | n = 415 |

* P <0.001 vs. baseline; mixed model for repeated measures.
† Scored 0-10, where 0 = no pain at all, and 10 = pain as bad as it can be.
There were no significant differences between the lasmiditan doses.

Patients randomized to either lasmiditan 100 mg or lasmiditan 200 mg had, on average, severe migraine disability at baseline (mean MIDAS score 21+). Patients showed a large, clinically meaningful improvement in MIDAS over 12 months of treatment (summarized in FIG. 3). Migraine disability, headache days and headache pain in the past 3 months improved over time with both doses. There were no significant differences between the lasmiditan doses for any outcome. Changes from baseline in the completers analysis were similar to results from overall population at each of the time points. This result suggests that the overall conclusion is not impacted by missing data/selective attrition.

Lasmiditan treatment led to decreases over time in MIDAS migraine disability scores, the number of headache days, and migraine severity, and these long-term effects were similar in lasmiditan 100 mg and 200 mg groups. The observed reduction in disability over several months, for example up to 12 months, surprisingly and unexpectedly leads to the concept that chronic administration of lasmiditan, preferably nightly, represents a means to achieve a persistent, disease modifying, reduction in migraine susceptibility in certain migraine patients. Thus, the inventions disclosed herein are supported by the unexpected observations from the Gladiator study of lasmiditan.

Example 3: Chronic Nightly Lasmiditan for Migraine Prevention

This study will test the primary hypothesis that chronic nightly lasmiditan is superior to placebo in the prevention in patients with therapy resistant migraine. A similar study can be conducted in migraine patients without the added criteria that they have failed prior prevention attempts. The primary endpoint of this study is the overall mean change from baseline in the number of monthly migraine headache days during the 3-month double-blind treatment phase in the total population (episodic and chronic migraine).

All key secondary objectives will be tested in both the total population (episodic and chronic migraine) and the episodic migraine subpopulation unless otherwise specified. The specific methodology (including testing order and population) for the tests of the following key secondary endpoints will be specified in the statistical analysis plan.

A secondary objective of the study is to compare chronic nightly lasmiditan with placebo with respect to the prevention of migraine in the episodic migraine subpopulation where the secondary objective reflects the overall mean change from baseline in the number of monthly migraine headache days during the 3-month double-blind treatment phase in patients with episodic migraine. A secondary objective of the study is to compare chronic nightly lasmiditan with placebo with respect to 50% response rate where the secondary objective reflects the percentage of patients with ≥50% reduction from baseline in monthly migraine headache days during the 3-month double-blind treatment phase. A secondary objective of the study is to compare chronic nightly lasmiditan with placebo with respect to change in functioning where the secondary objective reflects the mean change from baseline in the Role Function-Restrictive domain score of the Migraine-Specific Quality of Life Questionnaire version 2.1 (MSQ v2.1) at Month 3. A secondary objective of the study is to compare chronic nightly lasmiditan with placebo with respect to 75% response rate where the secondary objective reflects the percentage of patients with ≥75% reduction from baseline in monthly migraine headache days during the 3-month double-blind treatment phase. A secondary objective of the study is to compare chronic nightly lasmiditan with placebo with respect to 100% response rate where the secondary objective reflects the percentage of patients with 100% reduction from baseline in monthly migraine headache days during the 3-month double-blind treatment phase.

This study can be a multicenter, randomized, double-blind, parallel, placebo-controlled study of chronic nightly lasmiditan in patients who meet International Classification of Headache Disorders (ICHD) criteria for a diagnosis of migraine with or without aura or chronic migraine, and who have previously failed 2 to 4 standard-of-care treatments for migraine prevention. The study has 4 periods, including a prospective baseline period to determine patient eligibility.

The study has six treatment arms: chronic nightly lasmiditan (25, 50, 75, 100, 150, and 200 mg/nightly) and placebo. Following a 1-month prospective baseline period, eligible patients will be randomized in a 1:1 ratio to receive placebo or chronic nightly lasmiditan for up to 3 months of double-blind treatment. Nightly lasmiditan is administered orally, in one administration, by one or more tablets to achieve the specified dose being studied. Patients who complete the double-blind treatment phase may enter a 3-month open-label treatment phase. Thereafter, all patients in the open-label treatment phase will receive chronic nightly lasmiditan at the dose specified per arm.

The study will screen an estimated 764 potential study participants to ensure randomization of approximately 420 patients with migraine, of which approximately 250 patients have episodic migraine, or these numbers are adjusted as needed for the number of arms studied. Unless otherwise specified, statistical analyses will be conducted on an intent-to-treat (ITT) population, which includes all patients who are randomized and receive at least one dose of investigational product. Patients in the ITT population will be analyzed according to the treatment group to which they are randomized. When change from baseline is assessed, the patient will be included in the analysis only if he/she has a baseline and a post-baseline measurement. The primary analysis will evaluate the efficacy of chronic nightly lasmiditan compared with placebo on the overall mean change from baseline in the number of monthly migraine headache days and probable migraine headache days during the 3-month double-blind treatment phase. The primary analysis will be performed using a restricted maximum likelihood-based mixed model repeated measures technique.

Patients are eligible to be included in the study only if they meet all of the following criteria at screening: 1) are 18 to 75 years of age (inclusive) at the time of screening; 2) have a diagnosis of migraine as defined by International Headache Society ICHD-3 guidelines (1.1, 1.2, or 1.3) (ICHD-3 2018), with a history of migraine headaches of at least 1 year prior to visit 1, and migraine onset prior to age 50; 3) have a history, prior to visit 1, of at least 4 migraine headache days and at least 1 headache-free day per month on average within the past 3 months; 4) have, prior to visit 1, documentation (medical or pharmacy record or by physician's confirmation) of previous failure to 2 to 4 migraine preventive medication categories in the past 10 years from the following list due to inadequate efficacy (that is, maximum tolerated dose for at least 2 months) and/or safety/tolerability reasons, the list including (a) propranolol or metoprolol (b) topiramate, (c) valproate or divalproex, (d) amitriptyline, (e) flunarizine, (f) candesartan, (g) botulinum toxin A or B, and (h) medication locally approved for the prevention of migraine (patients only qualifying under (f) and (h) should not exceed 20% of the total study population); 5) from visit 2 to visit 3 (prospective baseline period), have a frequency of 4 or more migraine headache days and at least 1 headache-free day per 30-day period (to avoid biased reporting, patients will not be told the number of migraine or headache days on which study qualification is based); and 6) from visit 2 to visit 3 (prospective baseline period), must achieve sufficient compliance with ePRO daily headache entries as demonstrated by completion of at least 80% of daily diary entries.

It is believed that the chronic nightly administration of lasmiditan for use in the prevention of migraine will be superior to prior preventative therapies, particularly in certain previously unsuccessfully treated populations, by persistent action on the trigeminal nervous system. It is believed these pharmacological properties will result in superior efficacy for migraine prevention in patients who suffer from therapy resistant migraines. Thus, potential efficacy provided by the present use of lasmiditan, for preventing migraine in patients whose disease has been refractory to two or more prior monotherapy and/or dual therapy treatment or prevention regimens, would represent an important additional advancement in migraine prevention. Preferably, the patients treated by the dosing regimens of the present invention may potentially experience freedom from migraine pain, and/or freedom from migraine disability as assessed by methods well known to the skilled artisan, such as the MIDAS assessment or by well-known quality of life measures. Preferably patients treated with the dosing regimens of the present invention would experience three or less migraine days per month, and more preferably not more than one migraine day per month. Preferably, the dosing regimens of the present invention will provide improved migraine prevention as described herein, while at the same time demonstrating desirable clinical safety and tolerability.

Example 4: Study LAIL—A Phase 2, Randomized, Double-Blind, Controlled Trial of Once-Nightly Lasmiditan for Preventive Treatment of Episodic Migraine in Adults In Study LAIL, Lasmiditan will be administered once daily at least 8 hours before the need to drive, and dosing will be recommended at bedtime. As used herein this reflects a nightly regimen. Patients should not drive or engage in other activities requiring heightened attention until at least 8 hours after taking each dose of study drug, even if they feel well enough to do so. To minimize these effects, it is recommended that patients take study drug doses at bedtime. When possible based on the 8-hour restriction, dosing is recommended at bedtime. This regimen provides an example of "nightly" dosing as used herein, which can include any particular time of day where the patient intends to sleep or rest for some period of hours, as the patient would typically take as sleep time, and wherein preferably "nightly administration" will occur 8 hours prior to the next window in which the patient desires to operate an automobile. This regimen also provides an example of "nightly" dosing as used herein which means lasmiditan is administered one time every 24-hour period, or one time every calendar day, preferably for not less than 5 consecutive days, or preferably for a period of not less than 10 days, or for as long as needed for migraine prevention. This regimen also provides an example of "chronic" dosing as used herein which means lasmiditan is administered on an ongoing consecutive basis, where the patient administers the doses and/or wherein the patient is instructed to administer the doses as part of a treatment regimen.

| Objectives[a] | Endpoints[b] |
|---|---|
| Primary | |
| To test the hypothesis that at least 1 dose of lasmiditan (50 mg/day or 100 mg/day) is superior to placebo in the prevention of migraine headache in patients with episodic migraine | The overall mean change from baseline in the number of monthly migraine headache days during the 3-month double-blind treatment phase |
| Key Secondary Objectives If lasmiditan (50 or 100 mg/day) is statistically significantly superior to placebo on the primary objective, the following key secondary objectives will be tested controlling for multiplicity: | The specific methodology (including testing order, relationship and type I error allocation and propagation) for the tests of the following key secondary endpoints will be specified in a statistical analysis plan (SAP): |
| To compare lasmiditan with placebo with respect to: | |
| 50% response rate | The percentage of patients with ≥50% reduction from baseline in monthly migraine headache days |
| functioning | The mean change from baseline in the Role Function-Restrictive domain score of the MSQ v2.1 at Month 3 |

-continued

| Objectives[a] | Endpoints[b] |
|---|---|
| the number of monthly days with acute (abortive) migraine treatment use | The overall mean change from baseline in the number of monthly days with acute headache medication use |
| sleep | The overall mean change from baseline in the patient-reported outcome measure of sleep (PROMIS-SF v1.0 Sleep Disturbance 4a) |
| Other Secondary Objectives | Endpoints |
| To compare lasmiditan with placebo with respect to: | |
| 30% response rate | The percentage of patients with ≥30% reduction from baseline in monthly migraine headache days |
| 75% response rate | The percentage of patients with ≥75% reduction from baseline in monthly migraine headache days |
| 100% response rate | The percentage of patients with a 100% reduction from baseline in monthly migraine headache days |
| onset of 50% sustained response | The initial month at which statistical separation in the proportion of patients meeting at least a 50% reduction in monthly migraine headache days that is maintained at all subsequent months through Month 3 |
| moderate to severe headache days | The overall mean change from baseline in the number of monthly moderate to severe headache days |
| onset of effect | The initial month at which statistical separation in mean change from baseline in the number of monthly migraine headache days is demonstrated and maintained at all subsequent months through Month 3 |
| monthly headache days | The overall mean change from baseline in the number of monthly headache days |
| ICHD-3 migraine headache days | The overall mean change from baseline in the number of monthly ICHD-3 migraine headache days |
| monthly migraine headache hours | The overall mean change from baseline in the number of monthly migraine headache hours |
| monthly headache hours | The overall mean change from baseline in the number of monthly headache hours |
| disability and health-related quality of life | Changes from baseline to Month 3 on the following measures:<br>MIDAS total score and individual items<br>MSQ v2.1 total score, and Role Function-Preventive and Emotional Function domain score |
| patient global impression of severity and change of migraine condition | The mean change from baseline in the PGI-S score at Month 3<br>The mean PGI-C score at Month 3 |
| allodynia symptoms | The mean change from baseline in the ASC-12 score at Month 3 |
| migraine attacks | The overall mean change from baseline in the number of monthly migraine attacks |
| onset of migraine attacks after dosing | The overall mean difference in the timing of the onset of migraine attacks |
| | To assess: |
| the pharmacokinetics of lasmiditan | Mean plasma concentrations of lasmiditan |
| changes in efficacy, safety, and functional outcomes | During Study Period IV (follow-up):<br>Mean changes in all continuous measures of efficacy, safety, and functional outcomes that are also assessed in the double-blind treatment period |
| Tertiary Objectives | Endpoints |
| To compare lasmiditan with placebo with respect to: | |
| symptoms associated with migraine | The overall mean change from baseline in the number of monthly migraine headache days with:<br>nausea and/or vomiting<br>photophobia and phonophobia<br>aura |

-continued

| Objectives[a] | Endpoints[b] |
|---|---|
| | prodromal symptoms<br>The overall mean change from baseline in the number of monthly symptom-free days and headache-free days |
| symptoms of depression and anxiety | Mean changes from baseline to Month 3 on the following measures:<br>PHQ-9<br>GAD-7 |
| changes in health-related quality of life | Changes from baseline to Month 3 on the following measures:<br>HCRU<br>Employment status |

Abbreviations: ASC-12=12-item Allodynia Symptoms Checklist; GAD=7-item Generalized Anxiety Disorder Scale: HCRU=Health Care Resources Utilization questionnaire: ICHD=International Classification of Headache Disorders; MIDAS=Migraine Disability Assessment; MSQ v2.1=Migraine-Specific Quality of Life Questionnaire version 2.1; PGI-S=Patient Global Impression of Severity; PHQ-9=Patient Health Questionnaire-9; PROMIS-SF=Patient-Reported Outcomes Measurement Information System Short Form [v1.0 Sleep Disturbance 4a]; SAP=Statistical Analysis Plan.

[a] All the objectives are for the Study Period III (3-month double-blind treatment period), unless specified "during Study Period IV" in this table.

[b] Definitions of baseline and endpoint will vary depending on the assessment. For the primary and key secondary objectives, the baselines and endpoints are defined in Section 9. For the rest of the assessments, baselines and endpoints will be defined in the SAP.

Migraine and Headache Endpoint Definitions

| Endpoint | Definition/Criteria |
|---|---|
| Migraine headache | A headache, with or without aura, of ≥30 minutes duration, with both of the following required features (A and B):<br>A. At least 2 of the following headache characteristics:<br>Unilateral location<br>Pulsating quality<br>Moderate or severe pain intensity<br>Aggravation by or causing avoidance of routine physical activity<br>AND<br>B. During headache at least one of the following:<br>Nausea and/or vomiting<br>Photophobia and phonophobia<br>(Definition adapted from the standard IHS ICHD-3 definition) |
| Probable migraine headache | A headache of ≥30 minutes duration, with or without aura, but missing one of the migraine features in the IHS ICHD-3 definition. To be exact, it meets either at least two A criteria and zero B criteria, or one A criteria and at least one B criteria. |
| Migraine headache day (primary objective) | A calendar day on which a migraine headache or probable migraine headache occurs. |
| ICHD migraine headache day | A calendar day on which a migraine headache occurs. |
| Migraine headache attack | Beginning on any day a migraine headache or probable migraine headache is recorded and ends when a migraine-free day occurs. |
| Non-migraine headache | All headaches of ≥30 minutes duration not fulfilling the definition of migraine or probable migraine. |
| Non-migraine headache day | A calendar day on which a non-migraine headache occurs. |
| Headache day | A calendar day on which any type of headache occurs (including migraine, probable migraine, and non-migraine headache). |

Abbreviations: ICHD=International Classification of Headache Disorders; IHS=International Headache Society.

Overall Design:

Study LAIL is a Phase 2, multicenter, double-blind, randomized, placebo-controlled study of lasmiditan in adult patients with episodic migraine. The study will consist of 4 sequential periods (see FIG. 4 and Schedule of Activities below):

Study Period I (Screening): 3-30 days
Study Period II (Prospective Baseline): 30-40 days after Study Period I
Study Period III (Double-Blind Treatment): approximately 90 days
Study Period IV (Follow-Up): up to 32 days During Study Period III, Patients will be randomly assigned, with 2:1:1 ratio, to 1 of 3 once-daily (QD) oral treatments:
Placebo
Lasmiditan
50 mg
100 mg (see Section 6.1 about the titration approach for this treatment group)

Schedule of Activities (SoA):

During the treatment period, unscheduled visits may be conducted at the discretion of the investigator. The eligibility period of the prospective baseline assessment will last from 30 to 40 days. Investigators and patients may have up to an additional 5 days to schedule their Visit 3 appointment (beyond the 40 days); however, eligibility will be based on the 30- to 40-day period. The early termination visit (ET) activities apply to early terminations occurring prior to Visit 7. Visit 801 will be a phone visit; it will occur 7 days after Visit 7 or ET. Visit 801 will be used to assess any withdrawal symptoms and AEs associated with the study treatment, as well as any other planned assessments per the Schedule of Activities. Other assessments (including laboratory tests and additional follow-up visits) may be triggered by the observed AEs, as needed in the opinion of the investigator.

| Procedure | SP I Visit 1 Screening | SP II Visit 2 Prospective Baseline | SP III Treatment Period (3 months) | | | | | | SP IV Follow-Up | | Notes |
|---|---|---|---|---|---|---|---|---|---|---|---|
| | | | Visit 3 | Visit 4 | Visit 5 | Visit 6 | Visit 7 | ET | Visit 801 | Visit 802 | |
| Study Month | | −1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Assessments and Procedures | | | | | | | | | | | |
| Informed consent | X | | | | | | | | | | |
| Demographics | X | | | | | | | | | | |
| Migraine characteristics per IHS criteria | X | | | | | | | | | | |
| Migraine history | X | | | | | | | | | | |
| Full physical examination | X | | | | | | X | X | | | |
| Height | X | | | | | | | | | | |
| Weight | X | | X | | | | X | X | | | |
| Medical history | X | | | | | | | | | | |
| Substance use | X | | | | | | | | | | Substance: alcohol, caffeine, nicotine, tobacco |
| 12-lead ECG | X | | | X | | | X | X | | | Performed before blood draw. |
| Study Month | | −1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Vital signs | X | | X | X | X | X | X | X | | X | Includes sitting blood pressure and pulse, measured in |

| Procedure | SP I Visit 1 Screening | SP II Visit 2 Prospective Baseline | SP III Treatment Period (3 months) | | | | | | SP IV Follow-Up | | Notes |
|---|---|---|---|---|---|---|---|---|---|---|---|
| | | | Visit 3 | Visit 4 | Visit 5 | Visit 6 | Visit 7 | ET | Visit 801 | Visit 802 | |
| | | | | | | | | | | | triplicate. Predose and prior to blood draws. |
| Inclusion and exclusion criteria | X | | | | | | | | | | |
| Confirm eligibility | | X | X | | | | | | | | |
| AE review | | X | X | X | X | X | X | X | X | X | |
| Concomitant medication review | X | X | X | X | X | X | X | X | X | X | |
| Introduce eDiary, including assessment of patient's capability to use eDiary | X | | | | | | | | | | |
| Provide patient eDiary and patient paper log, as well as eDiary training | | X | | | | | | | | | |
| Study Month | | −1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | ±2 | ±2 | ±2 | ±2 | ±2 | | ±2 | ±2 | |
| Allowable range (days) between visits | 3-30 | 30-40 | | | | | | | | | |
| Patient training video | | | X | | | | | | | | If available and where local regulation and Ethical Review Boards allow, patients will watch a training video designed to address patient expectations with regard to participation in a placebo-controlled trial and the difference between medical treatment and research. |
| Dispense study treatment | | | X | X | X | X | | | | | |
| Study Month | | −1 | 0 | N/A | 1 | 2 | 3 | | | 4 | |
| Target interval (days) since previous visit | | | 30-45 | 7 | 23 | 30 | 30 | | 7 | 23 | |

-continued

| Procedure | SP I Visit 1 Screening | SP II Visit 2 Prospective Baseline | Visit 3 | Visit 4 | Visit 5 | Visit 6 | Visit 7 | ET | SP IV Follow-Up Visit 801 | Visit 802 | Notes |
|---|---|---|---|---|---|---|---|---|---|---|---|
| Interval allowance (days) | | | | ±2 | ±2 | ±2 | ±2 | | ±2 | ±2 | |
| Allowable range (days) between visits | 3-30 | 30-40 | | | | | | | | | |
| Patient eDiary enry | | | | | see details. | | | | | | Patients will complete the eDiaries daily starting at Visit 2. For details about the patient eDiary. |
| Patient paper log entry | | | | | see details. | | | | | | Patients will use the paper log, as needed, to record their use of concomitant medications for headache. For details about the patient paper log. |
| eDiary and patient paper log review | | | X | X | X | X | X | X | | X | |
| Randomization | | | X | | | | | | | | |
| Study Month | | −1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Assess study drug compliance | | | | X | X | X | X | X | | | |
| Collect unused/empty study drug pack | | | | X | X | X | X | X | | | |
| Clinical Laboratory Tests and Sampling Schedule | | | | | | | | | | | |
| Hematology | X | | | X | | X | | X | X | | |
| Clinical chemistry | X | | | X | | X | | X | X | | Fasting is not required. |
| Urinalysis | X | | | | | | | X | X | | |
| FSH | X | | | | | | | | | | Females only, if needed, to confirm menopausal status |

| Procedure | SP I<br>Visit 1<br>Screening | SP II<br>Visit 2<br>Prospective<br>Baseline | SP III<br>Treatment Period<br>(3 months) | | | | | | SP IV<br>Follow-Up | | Notes |
|---|---|---|---|---|---|---|---|---|---|---|---|
| | | | Visit 3 | Visit 4 | Visit 5 | Visit 6 | Visit 7 | ET | Visit 801 | Visit 802 | |
| Study Month | | -1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Serum pregnancy Test | X | | | | | | X | X | | | Serum pregnancy test to be performed only on women of child bearing potential. A positive urine test must be followed by a serum pregnancy test for confirmation. Collect serum pregnancy at Visit 7 or ET if patient not continuing into Study Period IV. |
| Study Month | | -1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Urine pregnancy Test | | | X | | X | X | | | | X | Urine pregnancy test to be performed only on women of child bearing potential. Done locally. A positive urine test must be followed by a serum pregnancy test for confirmation. |

-continued

| Procedure | SP I<br>Visit 1<br>Screening | SP II<br>Visit 2<br>Prospective<br>Baseline | SP III<br>Treatment Period<br>(3 months) | | | | | | SP IV<br>Follow-Up | | Notes |
|---|---|---|---|---|---|---|---|---|---|---|---|
| | | | Visit 3 | Visit 4 | Visit 5 | Visit 6 | Visit 7 | ET | Visit 801 | Visit 802 | |
| Urine Drug Screen | X | | | | | | | | | | |
| Pharmacogenetics sample | | | X | | | | | | | | Predose |
| Exploratory biomarker samples | | | X | | | | X | X | | | Visit 3: predose |
| Study Month | | -1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Pharmacokinetics | | | | X | X | X | | | | | Visit 6: An additional PK sample will be collected using microsampling technique. |

| Scales Questionnaires, and Outcome Measures |||||||||||||

| C-SSRS Baseline/Screening visit | X | | | | | | | | | | |
|---|---|---|---|---|---|---|---|---|---|---|---|
| C-SSRS Since Last Visit | | X | X | X | X | X | X | X | X | X | |
| Self-Harm Supplement Form | X | X | X | X | X | X | X | X | | X | Administration triggered only by spontaneously reported events. |
| Study Month | | -1 | 0 | N/A | 1 | 2 | 3 | | | 4 | |
| Target interval (days) since previous visit | | | 30-45 | 7 | 23 | 30 | 30 | | 7 | 23 | |
| Interval allowance (days) | | | | ±2 | ±2 | ±2 | ±2 | | ±2 | ±2 | |
| Allowable range (days) between visits | 3-30 | 30-40 | | | | | | | | | |
| Self-Harm Follow-up Form | X | X | X | X | X | X | X | X | | X | Required if triggered by the self-harm supplement form per instructions. |
| MIBS-4 | | | X | | X | X | X | X | | X | |
| MSQ v2.1 | | | X | | X | X | X | X | | X | |
| PGI-S | | | X | | X | X | X | X | | | |
| PGI-C | | | | | | | X | X | | | |
| GAD-7 | | | X | | | | X | X | | X | |
| PHQ-9 | | | X | | | | X | X | | X | |
| PROMIS-SF v1.0 Sleep Disturbance 4a | | | X | | X | X | X | X | | X | |
| ASC-12 | | | X | | | | X | X | | | |
| Assessment of Driving Accidents/Violations-Baseline Visit | | | X | | | | | | | | |

-continued

| Procedure | SP I<br>Visit 1<br>Screening | SP II<br>Visit 2<br>Prospective<br>Baseline | SP III<br>Treatment Period<br>(3 months) | | | | | SP IV<br>Follow-Up | | Notes |
|---|---|---|---|---|---|---|---|---|---|---|
| | | | Visit 3 | Visit 4 | Visit 5 | Visit 6 | Visit 7 ET | Visit 801 | Visit 802 | |
| Assessment of Driving Accidents/Violations Since Last Visit | | | | X | X | X | X X | | X | |
| Study Month | | -1 | 0 | N/A | 1 | 2 | 3 | | 4 | |
| Target interval (days) since previous visit | | | 30-45 | 7 | 23 | 30 | 30 | 7 | 23 | |
| Interval allowance (days) | | | | ±2 | ±2 | ±2 | ±2 | ±2 | ±2 | |
| Allowable range (days) between visits | 3-30 | 30-40 | | | | | | | | |
| Non-migraine chronic pain assessment | | | X | | X | X | X X | | X | Questionnaire administered by clinician to assess other chronic pain conditions Post-Visit 3 assessments are only for those who have chronic pain condition identified at Visit 3. |

Abbreviations:
AE = adverse event;
ASC-12 = 12-item Allodynia Symptoms Checklist;
C-SSRS = Columbia-Suicide Severity Rating Scale;
ET = early termination;
FSH = follicular-stimulating hormone;
GAD-7 = 7-item Generalized Anxiety Disorder Scale;
IHS = International Headache Society;
MIBS-4 = 4-item Migraine Interictal Burden Scale;
MSQ v2.1 = Migraine-Specific Quality of Life Questionnaire version 2.1;
PGI-C = Patient Global Impression of Change;
PGI-S = Patient Global Impression of Severity;
PHQ-9 = Patient Health Questionnaire-9;
PK = pharmacokinetic;
PROMIS-SF = Patient-Reported Outcomes Measurement Information System Short Form [v1.0 Sleep Disturbance 4a];
SP = study period.

The length of the randomized treatment phase (3 months) is considered sufficient to assess the safety and efficacy of a migraine preventive medication and is consistent with regulatory requirements for compounds with similar indications for use and patient populations. Among patients randomly assigned to placebo in migraine prevention studies, placebo response at 3 months ranged from 14% to 31% (Speciali et al. 2010), highlighting the importance of comparisons of active study drug to placebo. Given the short half life of lasmiditan, drug concentration should be nominal by 2 days after cessation. Patients will be evaluated for withdrawal effects during the initial 7 days after treatment discontinuation. A 1-month post-treatment follow-up period is included to continue to evaluate patient safety and frequency of migraines.

Two dose strengths of lasmiditan will be studied in this Phase 2 study: 50 mg and 100 mg. Systemic exposure with lasmiditan 50 mg and 100 mg is predicted to achieve or exceed the exposure observed in rats receiving an oral dose of 1 mg/kg lasmiditan that resulted in positive and statistically significant effects in various rat pharmacological models believed to be relevant to migraine. Doses of lasmiditan 100 mg are anticipated to maintain mean unbound brain concentrations above the in vitro inhibitory constant of the $5\text{-HT}_{1F}$ receptor for greater duration than that of lasmiditan 50 mg, which may provide greater efficacy for lasmiditan 100 mg relative to lasmiditan 50 mg. While lasmiditan efficacy on 2-hour pain freedom in the completed single-attack Phase 3 studies of lasmiditan appeared to be dose related, the recurrence rates of migraine were similarly low across the 50-mg to 200-mg dose range in the 2-hour to 24-hour time frame after dosing. In the long-term open-label study with intermittent treatment of migraine attacks with lasmiditan, a decrease over the 12-month treatment period was observed in migraine disability, headache days, headache severity, and number of migraines treated with lasmiditan. These findings were similar for the 100-mg and 200-mg doses.

TEAEs reported with lasmiditan from the completed single-attack Phase 3 studies were primarily neurologic in nature, mostly mild or moderate in severity, and the probability of experiencing TEAEs generally increased with increasing lasmiditan dose. Based on the studies of lasmiditan for acute treatment of migraine, lasmiditan 100 mg and 200 mg showed similar efficacy on endpoints that may be related to preventive treatment of migraine, but 200-mg dosing showed numerically more TEAEs. This Phase 2 study will test lasmiditan 50 mg and 100 mg for once-daily use in the preventive treatment of migraine.

Dose Regimen:

Lasmiditan will be administered once daily/nightly at least 8 hours before the need to drive, and dosing is recommended at bedtime. This treatment regimen is believed to maximize tolerability and the potential to observe efficacy of lasmiditan for prevention of migraine. In healthy volunteers, acute treatment with lasmiditan was shown to impair simulated driving performance in a dose-dependent manner, which resolved by 8 hours after dosing. As this is an important potential safety concern, patients participating in the LAIL study will be instructed not to drive vehicles for at least 8 hours after dosing. To allow for at least 8 hours before driving, dosing at around bedtime is recommended in this study. While the TEAEs reported with lasmiditan are generally mild to moderate and short in duration, a bedtime dosing recommendation is conceived to mitigate potential tolerability issues observed with intermittent, acute treatment of lasmiditan, which are considered to be less acceptable with chronic nightly preventive treatment. This includes TEAEs (e.g. somnolence, lethargy, or fatigue), which may be considered bothersome during wakeful hours. Another consideration supporting a bedtime dosing recommendation is that migraine attacks peak during the early morning hours. An analysis of 3592 migraine attacks in 1696 adults showed that migraine attacks frequently begin between 4 and 9 AM (Fox and Davis 1998) with almost half of attacks beginning during this 5-hour window. While prolonged pharmacodynamic effects of lasmiditan are considered to be an advantage of the present dosing regimens, dosing at bedtime will provide higher drug concentrations in the morning hours, a peak time for occurrence of migraine attacks.

A patient is considered to have completed the study if he/she has completed all phases of the study including the last visit or the last scheduled procedure shown in the Schedule of Activities. The end of the study is defined as the date of the last visit or last scheduled procedure shown in the Schedule of Activities for the last patient.

Study Population:

All patients must meet the following selection criteria. Eligibility of patients for study enrollment will be based on the results of a screening medical history, physical examination, neurological examination, clinical laboratory tests, electrocardiograms (ECGs), and migraine history during screening and a prospective baseline period, as described in the Inclusion and Exclusion Criteria sections. The nature of any comorbid conditions present at the time of the physical examination and any pre-existing conditions must be documented. Individuals who do not meet the criteria for participation in this study (screen failure) for specific reasons as outlined may be considered for rescreening once.

Patients are eligible to be included in the study only if all of the following criteria apply:
1. Patients must be 18 to 75 years of age inclusive, at the time of signing the informed consent.
2. Have a diagnosis of migraine with or without aura as defined by International Headache Society (IHS) International Classification of Headache Disorders guidelines (1.1, 1.2.1) (ICHD-3 2018), with a history of migraine headaches of at least 1 year prior to Visit 1, and migraine onset prior to age 50.
3. Prior to Visit 1, have a history of 4 to 14 migraine headache days and at least 2 migraine attacks per month on average within the past 3 months.
4. From Visit 2 to Visit 3 (prospective baseline period), have a frequency of 4 to 14 migraine headache days and at least 2 migraine attacks (see definitions) per electronic diary entries. To avoid biased reporting, patients are not be told the number of migraine headache days on which study qualification is based.
5. From Visit 2 to Visit 3 (prospective baseline period), patients must achieve sufficient compliance with ePRO daily headache entries as demonstrated by completion of at least 80% of daily diary entries.
6. Patients must be capable of giving signed informed consent as described which includes compliance with the requirements and restrictions listed in the informed consent form (ICF) and in this protocol.
7. Patient must be reliable and willing to follow study procedures.
8. Women of child-bearing potential must test negative for pregnancy, and must agree to use a highly effective method of contraception.

Patients are excluded from the study if any of the following criteria apply:
9. Have prior use of lasmiditan, including those who have previously completed or withdrawn from this study.
10. Have known hypersensitivity to lasmiditan, or to any excipient of lasmiditan oral tablets, or any sensitivity to a ditan or known hypersensitivity to multiple drugs in the opinion of the investigator.
11. Have a history of using a CGRP monoclonal antibody for the prevention of migraines within 4 months of Visit 1.
12. Have a history of failure of greater than 4 classes of migraine preventive medications.
13. Have had no more than 9 doses of tripans per month in the 3 months prior to Visit 1 and ≤9 triptan doses during the prospective baseline period.
14. Are currently receiving medication or other treatments for the prevention of migraine headaches, in the opinion of the investigator. Botulinum toxin A and B that has been administered in the head or neck area for therapeutic use must be discontinued at least 3 months prior to Visit 2. Medication, nerve blocks, or device use (such as transcranial magnetic stimulation) in the head or neck area or for migraine prevention must be discontinued at least 30 days prior to Visit 2.
15. Have a history of persistent daily headache, cluster headache, or migraine subtypes including migraine with brainstem aura (basilar-type migraine) (1.2.2), hemiplegic (sporadic or familial) migraine (1.2.3), or retinal migraine (1.2.4), defined by IHS ICHD-3.
16. Have a history of headache (for example, cluster headache, Medication Overuse headache) other than migraine or tension-type headache as defined by IHS ICHD-3 within 3 months prior to randomization.
17. Prior to Visit 1, have a history of ≥15 headache days (migraine, probable migraine or any other headache)

per month on average during the past 3 months or are suspected of suffering from chronic migraine as defined by IHS ICHD-3.
18. Have a history of head or neck injury within 6 months prior to Visit 1.
19. Have a history of traumatic head injury associated with significant change in the quality or frequency of their headaches.
20. Have a positive urine drug screen for any substances of abuse at Visit 1.
21. Have a history of recurrent dizziness and/or vertigo including benign paroxysmal positional vertigo, Meniere's disease, vestibular migraine, and other vestibular disorders.
22. Have a significant renal or hepatic impairment in the opinion of the investigator or if they meet hepatic monitoring criteria.
23. Women who are breast-feeding.
24. Have an acute, serious, or unstable medical condition that, in the judgement of the investigator, indicates a medical problem that would preclude study participation (e.g., symptomatic bradycardia).
25. Are unwilling or unable to comply with the use of a data collection device.

Screen failures are defined as patients who consent to participate in the clinical study but are not subsequently randomly assigned to study treatment. Individuals who do not meet the criteria for participation in this study (screen failure) may be rescreened once only if: Patients are using a concomitant medication that requires a stable dose for a specific duration before Visit 2 and additional time is needed to meet the duration requirement. The interval between screening and rescreening must be at least 45 days or longer if required for the specified timeframes in the inclusion/exclusion criteria or concomitant medication list.

Study treatment is defined as any investigational treatment and/or placebo intended to be administered to a study participant (patient) according to the study protocol. This study involves double-blind treatment with lasmiditan 50 mg and 100 mg or placebo administered by mouth QD for the prevention of migraine headaches. Lasmiditan will be administered QD at least 8 hours before the need to drive, recommended at bedtime. To preserve blinding throughout the study, patients in all treatment groups will receive two tablets per day (one of each size) in a double dummy fashion in order to the guarantee blinding of study treatment QD.

| | Tablets Administered (QD) | | | |
|---|---|---|---|---|
| | Active | | Placebo | |
| Study Group | Lasmiditan 50 mg | Lasmiditan 100 mg[a] | Lasmiditan 50 mg matching placebo | Lasmiditan 100 mg matching placebo |
| Lasmiditan 50 mg | X | | | X |
| Lasmiditan 100 mg | | X | X | |
| Placebo | | | X | X |

[a]The initial lasmiditan dose will be titrated: During the first week of treatment, patients in this treatment group will receive 50 mg of lasmiditan QD, and then 100 mg QD after that.

Study drug will be administered at approximately the same time each day, and recommended administration will be at bedtime. Patients will record the date and time of select dose administrations in their eDiary. Dose modifications are not allowed in this study.

This is a double-blind study (i.e., both the patient and investigator will be blinded to the study treatment). The following stratification factors will be used: Geographical region or country, Migraine frequency at baseline (<8 vs ≥8 migraine headache days per month). Enrollment of patients with low-frequency migraine headaches (i.e., <8 migraine headache days/month) will be stopped if the number of such patients exceeded 176. If an investigator, site personnel performing assessments, or patient is unblinded, the patient must be discontinued from the study.

Patient's compliance with study treatment will be assessed at each visit. Methods for assessing compliance will include direct questioning and counting returned tablets. At each visit, status of investigational product compliance will be collected based on the percentage of tablets taken from the total prescribed.

Indication for use, dates of administration, and dosage of any medication or vaccine (including all over-the-counter or prescription medicines for migraine as well as other conditions, vitamins, and/or herbal supplements) that the patient is receiving at the time of study enrollment or receives during the study must be recorded, along with, reason for use, dates of administration including start and end dates, dosage information including dose and frequency, route of administration.

Patients will use their log, as needed, to record their use of concomitant medications for migraine. The study personnel should record all concomitant medications throughout the patient's participation in the study.

All doses of lasmiditan were associated with driving impairment in a study of healthy volunteers on a computer-based driving simulator. Patients should restrict their driving, operation of heavy machinery, or other similar activities after taking study drug as described in the ICF. To minimize these effects, it is recommended that patients take lasmiditan doses at bedtime. They must also wait at least 8 hours before driving, operating heavy machinery, or performing other similar activities.

Patients who discontinue the study or investigational product during the double-blind treatment phase (Study Period III) will proceed immediately to Study Period IV. Patients discontinuing from the investigational product prematurely for any reason should complete adverse event and other follow-up procedures of the protocol. Temporary discontinuation will not be allowed.

The eDiary diary will be used to collect the information for the primary efficacy assessment. In addition to the information collected via the eDiary and the patient log, assessments will be administered at the site according to the Schedule of Activities. Secondary Efficacy Assessments include the Migraine-Specific Quality of Life Questionnaire Version 2.1. MSQ v2.1 is a self-administered health status instrument that was developed to address the physical and emotional impact on functioning that is of specific concern to individuals suffering from migraine headaches. The instrument consists of 14 items that address 3 domains (Jhingran et al. 1998b): Role Function-Restrictive, Role Function-Preventive, and Emotional Function. The restrictive domain specifically measures disability as related to the impact on performance of normal activities, with the preventive domain addressing complete functional impairment, and the emotional domain assessing the feelings related to disabling monthly migraine headache days. Responses are given using a 6-point Likert-type scale, ranging from "none of the time" to "all of the time." Raw scores for each domain are computed as a sum of item responses, with the collective sum providing a total raw score that is then converted to a 0 to 100 scale, with higher scores indicating a better health status, and a positive change in scores reflecting functional improvement (Jhingran et al. 1998a; Martin et al. 2000). The instrument was designed with a 4-week recall period and is considered reliable, valid, and sensitive to change in functional impairment due to migraine (Jhingran et al. 1998b; Bagley et al. 2012).

Another secondary efficacy assessment will be The Patient-Reported Outcomes Measurement Information System (Sleep-Related Disturbance Short Form 4a) (PROMIS®). PROMIS® is part of a National Institutes of Health Roadmap initiative. Its stated goal is "to provide clinicians and researchers access to efficient, precise, valid, and responsive adult- and child-reported measures of health and well-being" (HealthMeasures 2013). The PROMIS initiative used modern measurement theory and a scientifically rigorous approach for instrument development involving quantitative, qualitative, and mixed methods. This approach yielded patient self-report item banks with excellent psychometric properties. The PROMIS-SD (HealthMeasures WWW) patient self-report item bank was developed through an iterative process of literature searches, collecting and sorting items, expert content review, qualitative patient research, and pilot testing. The resulting 27 items assess self-reported perceptions of sleep quality, sleep depth, and restoration associated with sleep. This includes perceived difficulties and concerns with getting to sleep or staying asleep, as well as perceptions of the adequacy of, and satisfaction with, sleep. The PROMIS-SD has demonstrated excellent measurement properties including internal consistency and convergent validity. Validity of the item bank was supported by moderate to high correlations with existing scales and by the ability to distinguish among those with and without sleep disorders (Buysse et al 2010). The PROMIS-SD has been tested and exhibited validity evidence (e.g., expected associations, discrimination among known groups) in a wide range of populations (Busse et al 2013, Cook et al 2012, Fenton et al 2011, Stachler et al 2014). Subsequent research using item analyses and clinical judgement reduced the 27-item scale to 8 items. The authors reported the 8-item version to have "greater measurement precision than the Pittsburgh Sleep Quality Index (PSQI)" (Yu et al 2012). Further item reduction produced a 4-item version (PROMIS-SF SD 4a). The resulting 4 items measure sleep quality, sleep initiation, problems with sleep, and restfulness. Research conducted by Jensen et al (2016) demonstrated the 4-item version to have adequate reliability and validity. Each question has 5 response options ranging in value from 1 to 5. For scoring, the total raw score is found by summing the values of the response to each question. With the total raw score calculated, the applicable score conversion table is used in PROMIS Sleep Disturbance Scoring Manual to translate the total raw score into a T-score for each participant. The T-score rescales the raw score into a standardized score with a mean of 50 and a standard deviation (SD) of 10. Higher score represents greater sleep disturbance.

Another secondary efficacy assessment can include a Migraine Disability Assessment (MIDAS). The MIDAS is a patient-rated scale that was designed to quantify headache-related disability over a 3-month period. This instrument consists of 5 items that reflect the number of days reported as missed, or with reduced productivity at work or home and social events. Each question is answered as the number of days during the past 3 months of assessment, ranging from 0 to 90, with the total score being the summation of the 5 numeric responses. A higher value is indicative of more disability (Stewart et al. 1999, 2001). This instrument is considered reliable and valid, and is correlated with clinical judgment regarding the need for medical care (Stewart et al. 1999, 2001). For clinical interpretability, 4 categorical grades were developed based on the total score: Grade 1 (0 to 5) is for little or no disability, Grade II (6 to 10) is for mild disability, Grade III (11 to 20) is for moderate disability, and Grade IV (21+) is for severe disability. The severe disability category has subsequently been subdivided into Grade IV-A (severe [21 to 40]) and Grade IV-B (very severe [41 to 270]) because a high proportion of patients with chronic migraine are in Grade IV (Blumenfeld et al. 2011). Two additional questions (A and B) collect information on the frequency of headaches and the intensity of the headache pain. These are not scored in the MIDAS questionnaire but are included to provide clinically relevant information that may aid in treatment and management decisions.

Another secondary efficacy assessment can include a Patient Global Impression of Severity. The Patient Global Impression of Severity (PGI-S) scale (Guy 1976) is a patient-rated instrumental that measures current illness severity. The PGI-S includes a range of possible responses, from 1 ("normal, not at all ill") to 7 ("extremely ill"). Patient Global Impression of Change can be another secondary efficacy assessment. The Patient Global Impression of Change (PGI-C) scale (Guy 1976) is a patient-rated instrument that measures the change in the patient's symptoms. It is a 7-point scale in which a score of 1 indicates that the patient is "very much better," a score of 4 indicates that the patient has experienced "no change," and a score of 7 indicates that the patient is "very much worse." Another secondary efficacy assessment can include a 12-Item Allodynia Symptoms Checklist. The ASC-12 (Lipton et al 2008) is a 12-item, validated, quantitative, and patient-completed instrument to measure the presence and severity of cutaneous allodynia in association with headache attacks. The tool was developed to provide graded responses rather than dichotomous (present/absent) responses. The ASC-12 asks how often the patient experiences increased pain or an unpleasant sensation on the skin during the most severe type of headache when engaging in each of the 12 items, such as combing hair, wearing eyeglasses, and exposure to heat or cold. Each of the 12 items has the following response options: does not apply to me (0 points), never (0 points), rarely (0 points), less than half the time (1 point) and half the time or more (2 points). The total score ranges from 0 to 24 and yields the following allodynia categories (Lipton et al 2008): none (0 to 2 points), mild (3 to 5 points), moderate (6 to 8 points) and severe (9 points or more).

Other efficacy assessments include the information collected via the eDiary and the patient log. The patients' response to their acute migraine medications will be recorded at the site. The descriptions of the other tertiary assessments are listed below.

The Patient Health Questionnaire-9 (PHQ-9) is a 9-item patient-completed instrument that was designed for detecting MDD and for measuring the severity of depressive symptoms (Kroenke et al. 2001). The 9 items pertain to the diagnostic criteria for MDD from the Diagnostic and Statistical Manual of Mental Disorders, Fourth Edition (DSM-IV) and are still applicable for Diagnostic and Statistical Manual of Mental Disorders, Fifth Edition (DSM-V): Anhedonia, Depressed mood, Trouble sleeping, Feeling tired, Change in appetite, Guilt, self-blame, or worthlessness, Trouble concentrating, Feeling slowed down or restless, and Thoughts of being better off dead or hurting oneself. Each item is rated on a 4-point scale (0=never, 1=several days, 2=more than half the time, 3=nearly every day) based on symptoms over the past 2 weeks. The overall score ranges from 0 to 27, with the levels of depression severity defined as follows: 0-4 minimal, 5-9 mild, 10-14 moderate, 15-19 moderately severe, and 20-27 severe. The instrument is considered reliable and valid for use in research and clinical settings (Kroenke et al. 2001), including in patients with migraine (Seo and Park 2015a).

The 7-Item Generalized Anxiety Disorder Scale (GAD-7) is a 7-item patient-completed questionnaire that was designed to screen for GAD and for measuring the severity of anxiety symptoms (Spitzer et al. 2006). The tool was developed based on symptom criteria for GAD in the DSM-IV (still applicable for DSM-V) as well as review of existing anxiety scales, with items addressing the following: Feelings of nervousness, Uncontrollable worrying, Excessive worrying, Trouble relaxing, Restlessness, Irritability, and Fearfulness. The patient identifies how much they have been bothered by these symptoms over the past 2 weeks. Each of the 7 items is rated on a 4-point scale (0=not at all, 1=several days, 2=more than half the days, 3=nearly every day), with total score ranging from 0 to 21. The levels of anxiety severity are defined as follows: 0-4=minimal, 5-9=mild, 10-14=moderate, and 15-21=severe. The instrument is considered reliable and valid for use in research and clinical settings (Spitzer et al. 2006), including in patients with migraine (Seo and Park 2015b).

Planned time points for all safety assessments are provided in the Schedule of Activities (SoA). A complete physical examination will include, at a minimum, assessments of the cardiovascular, respiratory, gastrointestinal, and neurological systems. Height and weight will also be measured and recorded. Investigators should pay special attention to clinical signs related to previous serious illnesses. Adverse Events (AEs) are recorded based on examinations. Vital signs will include body temperature, blood pressure, and pulse. Blood pressure and pulse will be measured in triplicate in the sitting position prior to blood draws and study drug administration. Height and weight will be assessed as indicated in the Schedule of Activities. Any clinically significant findings from vital signs measurement that result in a diagnosis should be reported as an AE.

For each patient, a single, 12-lead digital Electrocardiogram (ECG) will be collected at the visits shown in the Schedule of Activities. ECGs should be recorded according to the study-specific recommendations included in the ECG manual. The screening ECG will be read locally. The rest of the ECGs will be read centrally. Patients must be supine for approximately 5 to 10 minutes before ECG collection and remain supine but awake during ECG collection. Any clinically significant findings from ECGs that result in a diagnosis should be reported as an AE.

With the exception of laboratory test results that may unblind the study, the results of laboratory tests will be provided to the investigator. Appendix 2 provides a list of clinical laboratory tests to be performed and to the SoA for the timing and frequency. The investigator must review the laboratory report, document this review, and record any clinically relevant changes occurring during the study in the AE section of the CRF. Clinically significant abnormal laboratory findings are those which are not associated with the underlying disease, unless judged by the investigator to be more severe than expected for the participant's condition. All laboratory tests with values considered clinically significantly abnormal during participation in the study should be repeated until the values return to normal or baseline or are no longer considered clinically significant by the investigator or medical monitor. If such values do not return to normal/baseline within a period of time judged reasonable by the investigator, the etiology should be identified and the sponsor notified. All protocol-required laboratory assessments, as defined in Appendix 2, must be conducted in accordance with the laboratory manual and the SoA. Any clinically significant findings from laboratory tests that result in a diagnosis should be reported as an AE. If a study patient experiences elevated ALT≥3×ULN, ALP≥2×ULN, or elevated TBL≥2×ULN, liver testing should be repeated within 3 to 5 days including ALT, AST, ALP, TBL, direct bilirubin, gamma-glutamyl transferase, and creatine kinase to confirm the abnormality and to determine if it is increasing or decreasing. If the abnormality persists or worsens, clinical and laboratory monitoring should be initiated by the investigator and in consultation with the study medical monitor. Monitoring of ALT, AST, TBL, and ALP should continue until levels normalize or return to approximate baseline levels.

Because lasmiditan is a centrally penetrant drug, assessment of suicidal ideation and behavior will be monitored during the study using the Columbia Suicide-Severity Rating Scale (C-SSRS). C-SSRS is a scale that captures the occurrence, severity, and frequency of suicidal ideation and behavior during the assessment period via a questionnaire (Posner et al. 2011). The scale includes suggested questions to solicit the type of information needed to determine if a suicide-related thought or behavior occurred. The C-SSRS is administered by an appropriately trained healthcare professional with at least 1 year of patient care/clinical experience according to the Schedule of Activities.

To further evaluate the impact of lasmiditan on driving, patients will be asked to respond to questions related to motor vehicle accidents and moving violations according to the Schedule of Activities.

At the visits and times specified in the Schedule of Activities, venous blood samples will be collected to determine the plasma concentrations of lasmiditan and its metabolite(s). When a blood sample is drawn, the time (24-hour clock) and date of the last dose administration (typically from previous evening) prior to blood sampling should be recorded. The exact time and date of the blood sampling should also be recorded. A validated assay will be used to determine plasma concentrations of lasmiditan and its metabolite(s). Drug concentration information that may unblind the study will not be reported to investigative sites or blinded personnel until the study has been unblinded.

Health Care Resource Utilization and Employment Status (The HCRU) will be solicited by study personnel while documenting patient responses. The HCRU consists of 3 questions, asking about the number of hospital emergency room visits, overnight stays in a hospital, and any other visits with a healthcare professional that occurred since the patient's last study visit, outside of visits associated with their participation in the clinical trial. Patients will also be specifically asked about the number of healthcare events that are related to migraine headaches. The baseline visit will include the same questions, but with the frame of reference being over the last 6 months. A question on employment status will also be solicited, given the correlation and potential confounding with health outcomes measures, such as the MIDAS.

The primary hypothesis is to determine that at least 1 dose of lasmiditan (50 mg/day or 100 mg/day) is superior to placebo in the prevention of migraine headache in patients with episodic migraine. Approximately 541 patients will be screened to achieve 292 patients randomly assigned, with 2:1:1 ratio, to: placebo (n=146), lasmiditan 50 mg (n=73), or lasmiditan 100 mg (n=73). With the assumption of a 20% discontinuation rate and an effect size of 0.55, it is estimated that this sample size will provide approximately 90% power that the most effective dose of lasmiditan will separate from placebo at a 1-sided significance level of 0.05 or 0.1, or preferably at a 2-sided significance level of 0.05, for the intent-to-treat (ITT) population in this study.

Three analysis populations are defined as follows: ITT population, safety population, and follow-up population. The ITT and safety populations include all patients who are randomized and receive at least one dose of investigational product. The follow-up population includes all patients who enter the follow-up phase (Study Period IV). Unless otherwise stated, all efficacy analyses will be performed according to the ITT principle on the ITT population; that is, patients will be analyzed according to the treatment to which they were randomized, regardless of whether they actually received a different treatment. Safety analyses will be conducted on the safety population based on treatment the patient received. Analyses for the follow-up phase (Study Period IV) will be based only on the follow-up population. Unless otherwise specified, analyses will be conducted on the ITT population for efficacy analyses and on the safety population for safety analyses. When change from baseline is assessed, the patient will be included in the analysis only if he/she has a baseline and a postbaseline measurement. Continuous efficacy variables with repeated measures will be analyzed using mixed model repeated measures (MMRM) methods. The MMRM will include the fixed categorical effects of treatment, baseline migraine headache day frequency category (<8 vs ≥8 migraine headache days/month), pooled country, month, and treatment-by-month interaction, as well as the continuous fixed covariates of baseline and baseline-by-month interaction. For the model of the primary endpoint, the baseline migraine headache day frequency category will be excluded from the covariates since the continuous baseline monthly migraine headache day value is already in the model. For the analysis for Study Period III, Visit 3 is defined as the baseline and all the scheduled visits between Visit 5 and Visit 7 are defined as the post-baseline observations. For continuous efficacy variables without repeated measures, an analysis of covariance (ANCOVA) model with last observation carried forward (LOCF) imputation will be used, which contains the main effects of treatment, baseline migraine headache day frequency category, and pooled country, as well as the continuous fixed covariate of baseline. Type III sum-of-squares for the Least Squares Means (LSMeans) will be used for the statistical comparisons. For the analysis for Study Period III, Visit 3 is defined as the baseline and the last nonmissing observation between Visit 3 and Visit 7 will be the post-baseline observation. Binary efficacy variables with repeated measures will be analyzed using a generalized linear mixed model (GLIMMIX) as pseudo-likelihood-based mixed effects repeated measures analysis. The GLIMMIX model will include the fixed, categorical effects of treatment, month, and treatment-by-month interaction, as well as the continuous, fixed covariate of baseline value. For binary efficacy variables without repeated measures, comparisons between treatment groups will be performed using logistic regressions with the same model terms as the ANCOVA model. Pooled country may be removed to ensure model convergence. For continuous safety variables with repeated measures, MMRM methods will be used, as well as an ANCOVA model with LOCF imputation if deemed appropriate. When an ANCOVA model is used for safety measures, the model will contain the main effect of treatment, as well as the continuous fixed covariate of baseline. Type III sum-of-squares for the LSMeans will be used for the statistical comparisons. For categorical safety variables (such as AEs and other categorical changes of interest), as well as categorical baseline characteristics, comparisons between treatment groups will be performed using Fisher's exact test. Treatment effects will be evaluated based on a 2-sided significance level of 0.05 for all the efficacy and safety analyses unless otherwise stated. Type I error due to multiple comparisons for the primary and key secondary objectives will be controlled according to the multiple comparisons procedure defined in the SAP. There will be no adjustments for multiplicity for analyses of other data (other secondary objectives or tertiary objectives). Countries will be pooled as deemed necessary for statistical analysis purposes. Additional exploratory analyses of the data will be conducted as deemed appropriate.

The number and percentage of ITT patients who complete the study or discontinue early will be tabulated for all treatment groups for Study Period III. Reasons for discontinuation will be compared between treatment groups for Study Period III with the ITT population. In addition, subcategories of discontinuation due to patient decision will be summarized. For Study Period IV, the number and percentage of ITT patients who enter Study Period IV will be tabulated for all treatment groups as well as among these patients, the number and percentage patients who complete Study Period IV. Only descriptive statistics will be presented for the treatment groups in Study Period IV. Patient allocation by investigator will be summarized for Study Period III for all ITT patients. Patient allocation by investigator will also be listed for all study periods.

The following patient characteristics at baseline will be summarized by treatment group for all ITT patients. Demographic (age, sex, ethnic origin, height, weight, body mass index), Migraine and/or headache-related measures from the ePRO diary per 30-day baseline period, Alcohol, tobacco, caffeine, and nicotine consumption, Medical history and pre-existing conditions, Medical history and pre-existing conditions will be summarized by preferred term within system organ class (SOC).

The proportion of patients who received concomitant medication collected from eCRFs and the acute medications collected on the headache medication log will be summarized for all ITT patients for Study Period III and Study Period IV separately.

A patient will be considered overall compliant with investigational product during Study period III if all non-missing visit-wise compliance data from Visits 5 through 7 indicate compliance. The percentage of patients who are compliant with investigational product at each individual visit and overall will be compared between treatment groups using Fisher's exact test.

Electronic patient-reported outcomes diary compliance at each 1-month period (including baseline, Month 1, Month 2, Month 3, and Month 4) as well as for Study Period III overall (Month 1 through Month 3) will be calculated. Diary compliance at each period is calculated as:

$$\frac{\text{Actual number of diary days in the period}}{\text{Expected number of diary days in the period}} \times 100$$

The primary efficacy endpoint is the overall mean change from the baseline period in the number of monthly migraine headache days during the 3-month double-blind treatment phase (Study Period III), and the primary analysis will evaluate the efficacy of lasmiditan compared with placebo in the total ITT population. The primary analysis will be performed using a restricted maximum likelihood-based MMRM technique. The analysis will include the fixed categorical effects of treatment, pooled country, month, and treatment-by-month interaction, as well as the continuous fixed covariates of baseline number of migraine headache days and baseline number of migraine headache days-by-month interaction. An unstructured covariance structure will be used to model within-patient errors. The Kenward-Roger (Kenward and Roger 1997) approximation will be used to estimate denominator degrees of freedom. If the model does not converge with both the Hessian and the G matrix being positive definite under the default fitting algorithm used by PROC MIXED, the Fisher scoring algorithm will be implemented by specifying the SCORING option in SASR. If the model still fails to converge, the model will be fit using covariance matrices of the following order specified by a decreasing number of covariance parameters until convergence is met: Heterogeneous Toeplitz, Heterogeneous first-order autoregressive, Toeplitz, First-order autoregressive. When the unstructured covariance matrix is not utilized, the sandwich estimator (Diggle and Kenward 1994) will be used to estimate the standard errors of the fixed effects parameters. The sandwich estimator is implemented by specifying the EMPIRICAL option in SASR. When the sandwich estimator is utilized, the Kenward-Roger approximation for denominator degrees of freedom cannot be used. Instead, the denominator degrees of freedom will be partitioned into between-patient and within-patient portions by the DDFM=BETWITHIN option in SASR. SASR PROC MIXED will be used to perform the analysis.

The secondary measures will be analyzed using ITT population for the double-blind treatment phase (Study Period III). The analysis models for continuous secondary measures will be the same as for the primary analyses (Section 9.4.3.1) and the GLIMMIX model will be used for the analysis of the percentage of patients with ≥50% reduction from baseline in monthly migraine headache days.

To control for overall type I error, the primary and a subset of secondary objectives will be gated. The gated secondary analyses will be tested using a multiple comparisons procedure that preserves overall type I error at 2-sided alpha level of 0.05. If any of the null hypotheses are rejected for the primary endpoints, the gated secondary endpoints will be tested according to the multiple comparisons procedure.

Changes from baseline on the secondary and tertiary measures will be analyzed. Definitions of these baselines will be included in the SAP. In addition, categorical analysis for the frequency measure will be performed. There will be no adjustments for multiplicity for analyses of the other secondary or tertiary endpoints.

The safety and tolerability of treatment will be assessed by summarizing the following: TEAEs, SAEs, AEs leading to discontinuation, Vital signs and weight, ECGs, Laboratory measurements, C-SSRS, Driving accidents/violations, AEs related to withdrawal. Unless specified otherwise, the categorical safety analyses will include both scheduled and unscheduled visits. Comparisons between treatment groups for all categorical safety measures will be made using Fisher's exact test for Study Period III with the safety population. Descriptive statistics only will be presented for the analyses in Study Period IV. Analyses of continuous safety data will be conducted for Study Period III and Study Period III/IV using the safety population. In those analyses, only values collected at scheduled visits will be used.

Treatment-emergent adverse events are defined as the reported AEs that first occurred or worsened during the postbaseline phase compared with the baseline phase. For each TEAE, the reported severity level of the event (mild, moderate, or severe) will be determined by patient or physician opinion. The Medical Dictionary for Regulatory Activities (MedDRA) Lowest Level Term (LLT) will be used in the treatment-emergent computation. For each LLT, the maximum severity at baseline will be used as the baseline severity. If the maximum severity during postbaseline is greater than the maximum baseline severity, the event is considered to be treatment-emergent for the specific postbaseline period. Safety analyses for each study period will use all visits up through the last scheduled visit in the prior study period as baseline. For each patient and TEAE, the maximum severity for the MedDRA level being displayed (preferred term, High Level Term, or SOC) is the maximum postbaseline severity observed from all associated LLTs mapping to that MedDRA level. For events that are sex-specific, the denominator and computation of the percentage will include only patients from the specific sex.

Concentrations of lasmiditan and its metabolite(s) will be illustrated graphically and summarized descriptively, which may include a visual comparison of lasmiditan concentrations by collection method. A population approach may be used to characterize the PK of lasmiditan in patients with migraine, assess the magnitude of PK variability associated with bedtime dosing, and identify the potential factors that may have an impact on the PK. If necessary, data from other clinical studies evaluating lasmiditan may be combined with data from this study to support analyses. If warranted and based on availability of data, the exposure-response relationship of lasmiditan concentrations to efficacy endpoints and/or safety endpoints as well as the potential factors that may have an impact on these endpoints may also be explored. Additional analyses may be performed, if warranted.

The tests detailed below will be performed by the central laboratory. Protocol-specific requirements for inclusion or exclusion of patients are detailed in the protocol. Additional tests may be performed at any time during the study as determined necessary by the investigator or required by local regulations.

| Clinical Laboratory Tests |
|---|
| Hematology[a] |
| Hemoglobin |
| Hematocrit |
| Erythrocyte count (RBCs) |
| Mean cell volume |
| Mean cell hemoglobin |
| Mean cell hemoglobin concentration |
| Leukocytes (WBCs) |
| Differential |
| Neutrophils, segmented |
| Lymphocytes |
| Monocytes |
| Eosinophils |

Clinical Laboratory Tests

Basophils
Platelets
Cell Morphology
Urine Drug Screen (UDS)[a,b]
Urinalysis[a,c]

Specific gravity
pH
Protein
Glucose
Ketones
Bilirubin
Urobilinogen
Blood
Nitrite
Urine leukocyte esterase
Microscopic examination of sediment
Stored Samples[f]

Exploratory biomarker samples
Serum
Clinical Chemistry[a]

Sodium
Chloride
Bicarbonate
Potassium
Total bilirubin
Direct bilirabin
Total Protein
Alkaline phosphatase (ALP)

Clinical Laboratory Tests

Alanine aminotransferase (ALT)
Aspartate aminotransferase (AST)
Gamma-glutamyl transferase (GGT)
Blood urea nitrogen (BUN)
Creatinine
Creatinine kinase (CK)
Uric acid
Calcium
Glucose
Albumin
Cholesterol (total)
Triglyercides
Hormones (female)

Pregnancy (serum[a,b,d] and urine[e])
Follicle-Stimulating Hormone (FSH)[a,b,f]
Pharmacogenomics sample[g]
Pharmacokinetic (PK) samples[a,g] (lasmiditan concentration)

Abbreviations:
ALT = alanine aminotransferase; ALP = alkaline phosphatase; AST = aspartate aminotransferase; BUN = blood urea nitrogen; CK = creatine kinase; FSH = follicle-stimulating hormone; GGT = gamma-glutamyl transferase; PK = pharmacokinetics; RBC = red blood cell; WBC = white blood cell.
[a]Assayed by designated laboratory.
[b]Performed at screening only.
[c]Results will be confirmed by the central laboratory/other at the time of initial testing.
[d]Serum pregnancy test to be performed only on women of child bearing potential.
[e]Urine pregnancy test to be performed only on women of child bearing potential. Done locally and prior to dosing.
[f]Females only, if needed, to confirm menopausal status (details in Inclusion Criterion).
[g]Results will not be provided to the investigative sites.

| | Abbreviations |
|---|---|
| Term | Definition |
| 5-HT | 5-hydroxytryptamine |
| ACE | angiotensin-converting enzyme |
| AE | adverse event: Any untoward medical occurrence in a patient or clinical investigation subject administered a pharmaceutical product that does not necessarily have a causal relationship with this treatment. An adverse event can therefore be any unfavorable and unintended sign (including an abnormal laboratory finding), symptom, or disease temporally associated with the use of a medicinal (investigational) product, whether or not related to the medicinal (investigational) product. |
| ALP | alkaline phosphatase |
| ALT | alanine aminotransferase |
| ARB | angiotensin receptor blocker |
| ASC-12 | 12-item Allodynia Symptoms Checklist |
| AST | aspartate aminotransferase |
| blinding | A single-blind study is one in which the investigator and/or his staff are aware of the treatment but the patient is not, or vice versa, or when the sponsor is aware of the treatment but the investigator and/his staff and the patient are not. A double-blind study is one in which neither the patient nor any of the investigator or sponsor staff who are involved in the treatment or clinical evaluation of the patients are aware of the treatment received. |
| CGRP | calcitonin gene-related peptide |
| CIOMS | Council for International Organizations of Medical Sciences |
| complaint | A complaint is any written, electronic, or oral communication that alleges deficiencies related to the identity, quality, purity, durability, reliability, safety or effectiveness, or performance of a drug or drug delivery system. |
| compliance | Adherence to all study-related, good clinical practice (GCP), and applicable regulatory requirements. |
| COA/eCOA | clinical outcome assessment/electronic clinical outcome assessment |
| CONSORT | Consolidated Standards of Reporting Trials |
| CRP | clinical research physician: Individual responsible for the medical conduct of the study. Responsibilities of the CRP may be performed by a physician, clinical research scientist, global safety physician or other medical officer. |

-continued

| Abbreviations | |
|---|---|
| Term | Definition |
| CRS | clinical research scientist |
| C-CASA | Columbia Classification Algorithm of Suicide Assessment |
| C-SSRS | Columbia-Suicide Severity Rating Scale |
| DMC | data monitoring committee |
| DNA | deoxyribonucleic acid |
| ECG | electrocardiogram |
| EDC | electronic data capture |
| eCRF | electronic case report form |
| eDiary | electronic diary (i.e., an ePRO device referenced as eDiary) |
| enroll | The act of assigning a patient to a treatment. Patients who are enrolled in the study are those who have been assigned to a treatment. |
| enter | Patients entered into a study are those who sign the informed consent form directly or through their legally acceptable representatives. |
| ERB | Ethical Review Board |
| ET | early termination |
| EU | European Union |
| FSH | follicular-stimulating hormone |
| GAD-7 | 7-item Generalized Anxiety Disorder Scale |
| GAD | generalized anxiety disorder |
| GCP | good clinical practice |
| GLIMMIX | generalized linear mixed model |
| HIPAA | Health Insurance Portability and Accountability Act |
| IB | Investigator's Brochure |
| ICF | informed consent form |
| ICH | International Council for Harmonisation |
| ICHD | International Classification of Headache Disorders |
| IRS | International Headache Society |
| IQR | interquartile range |
| Informed consent | A process by which a patient voluntarily confirms his or her willingness to participate in a particular study, after having been informed of all aspects of the study that are relevant to the patient's decision to participate. Informed consent is documented by means of a written, signed and dated informed consent form. |
| interim analysis | An interim analysis is an analysis of clinical study data, separated into treatment groups, that is conducted before the final reporting database is created/locked. |
| investigational product | A pharmaceutical form of an active ingredient or placebo being tested or used as a reference in a clinical trial, including products already on the market when used or assembled (formulated or packaged) in a way different from the authorized form, or marketed products used for an unauthorized indication, or marketed products used to gain further information about the authorized form. |
| IRB/IEC | Institutional Review Board/Independent Ethics Committee |
| ITT | intention to treat: The principle that asserts that the effect of a treatment policy can be best assessed by evaluating on the basis of the intention to treat a patient (that is, the planned treatment regimen) rather than the actual treatment given. It has the consequence that patient allocated to a treatment group should be followed up, assessed, and analyzed as members of that group irrespective of their compliance to the planned course of treatment. |
| IWRS | interactive web-response system |
| LLT | Lowest Level Term |
| LOCF | last observation carried forward |
| LSMeans | least squares means |
| MAOI | monoamine oxidase inhibitor |
| MBS | most bothersome symptom |
| MDD | major depressive disorder |
| MedDRA | Medical Dictionary for Regulatory Activities |
| MD3S-4 | 4-item Migraine Interictal Burden Scale |
| MSQ v2.1 | Migraine-Specific Quality of Life Questionnaire version 2.1 |
| mITT | modified intent to treat |
| MMRM | mixed model repeated measures |
| NIMH | National Institute of Mental Health |
| NRI | norepinephrine reuptake inhibitor |
| NSAID | nonsteroidal anti-inflammatory drug |
| PGI-C | Patient Global Impression of Change |
| PGI-S | Patient Global Impression of Severity |
| PHQ-9 | Patient Health Questionnaire-9 |
| PK/PD | pharmacokinetics/pharmacodynamics |
| ePRO | electronic patient-reported outcomes |
| PROMIS-SF | Patient-Reported Outcomes Measurement Information System Short Form [v1.0 Sleep Disturbance 4a] |
| QD | once daily |
| QTcF | corrected QT interval (Fridericia's formula) |
| RNA | ribonucleic acid |

-continued

| Abbreviations | |
|---|---|
| Term | Definition |
| SAE | serious adverse event |
| SAP | statistical analysis plan |
| SAC | Statistical Analysis Center |
| screen | The act of determining if an individual meets minimum requirements to become part of a pool of potential candidates for participation in a clinical study. |
| SNRI | serotonin-norepinephrine reuptake inhibitor |
| SP | study period |
| SSRI | selective serotonin reuptake inhibitor |
| SUSARs | suspected unexpected serious adverse reactions |
| TBL | total bilirubin |
| TCA | tricyclic antidepressant |
| TENS | transcutaneous electrical nerve stimulation |
| TEAE | Treatment-emergent adverse event: An untoward medical occurrence that emerges during a defined treatment period, having been absent pretreatment, or worsens relative to the pretreatment state, and does not necessarily have to have a causal relationship with this treatment. |
| ULN | upper limit of normal |
| US | United States |

REFERENCES

Bagley C L, Rendas-Baum R, Maglinte G A, Yang M, Varon S F, Lee J, Kosinski M. Validating Migraine-Specific Quality of Life Questionnaire v2.1 in episodic and chronic migraine. *Headache.* 2012; 52(3):409-421.

Berger A, Bloudek L M, Varon S F, Oster G. Adherence with migraine prophylaxis in clinical practice. *Pain Pract.* 2012; 12(7):541-549.

Blumenfeld A M, Varon S F, Wilcox T K, Buse D C, Kawata A K, Manack A, Goadsby P J, Lipton R B. Disability, HRQoL and resource use among chronic and episodic migraineurs: results from the International Burden of Migraine Study (IBMS). *Cephalalgia.* 2011; 31(3):301-315.

Blumenfeld A M, Bloudek L M, Becker W J, Buse D C, Varon S F, Maglinte G A, Wilcox T K, Kawata A K, Lipton R B. Patterns of use and reasons for discontinuation of prophylactic medications for episodic migraine and chronic migraine: results from the Second International Burden of Migraine Study (IBMS-II). *Headache.* 2013; 53(4):644-655.

Bordini C A, Mariano da Silva H, Garbelini R P, Teixeira S O, Speciali J G. Effect of preventive treatment on health-related quality of life in episodic migraine. *J Headache Pain.* 2005; 6(5):387-391.

Breslau N, Schultz L, Lipton R, Peterson E, Welch K M. Migraine headaches and suicide attempt. *Headache.* 2012; 52(5):723-731.

Buse D C, Bigal M B, Rupnow M, Reed M, Serrano D, Lipton R. Development and validation of the Migraine Interictal Burden Scale (MIBS): A self-administered instrument for measuring the burden of migraine between attacks. *Neurology.* 2007; 68:A89.

Buse D C, Rupnow M F, Lipton R B. Assessing and managing all aspects of migraine: migraine attacks, migraine-related functional impairment, common comorbidities, and quality of life. *Mayo Clin Proc.* 2009; 84(5):422-435.

Busse M, Stromgren K, Thorngate L, Thomas K A. Parents' responses to stress in the neonatal intensive care unit. *Crit Care Nurse.* 2013; 33(4):52-59.

Buysse D J, Yu L, Moul D E, Germain A, Stover A, Dodds N E, Johnston K L, Shablesky-Cade M A, Pilkonis P A Development and validation of patient-reported outcome measures for sleep disturbance and sleep-related impairments. *Sleep.* 2010; 33(6):781-792.

[C-SSRS] The Columbia Lighthouse Project. The Columbia Protocol for Research. Columbia-Suicide Severity Rating Scale Scoring and Data Analysis Guide. Version 2.0. Available at: http://cssrs.columbia.edu/wp-content/uploads/ScoringandDataAnalysisGuide-for-Clinical-Trials-1.pdf. Accessed Jun. 13, 2019.

Cook K F, Bamer A M, Amtmann D, Molton I R, Jensen M P. Six patient-reported outcome measurement information system short form measures have negligible age- or diagnosis-related differential item functioning in individuals with disabilities. *Arch Phys Med Rehabil.* 2012; 93(7):1289-1291.

D'Amico D, Solari A, Usai S, Santoro P, Bernardoni P, Frediani F, De Marco R, Massetto N, Bussone G; Progetto Cefalee Lombardia Group. Improvement in quality of life and activity limitations in migraine patients after prophylaxis. A prospective longitudinal multicentre study. *Cephalalgia.* 2006; 26(6):691-696.

Diamond S, Bigal M E, Silberstein S, Loder E, Reed M, Lipton R B. Patterns of diagnosis and acute and preventive treatment for migraine in the United States: results from the American Migraine Prevalence and Prevention Study. *Headache.* 2007; 47(3):355-363.

Diggle P, Kenward M G. Informative drop-out in longitudinal data analysis. *J Royal Statist Soc Series C: Appl Statist.* 1994; 43(1):49-93.

[DSM-IV] American Psychiatric Association. *Diagnostic and Statistical Manual of Mental Disorders,* 4th edition (text revision). Washington, D C, 2000.

[DSM-V] American Psychiatric Association. *Diagnostic and Statistical Manual of Mental Disorders,* 5th edition. Arlington, VA, 2013.

Durham P L. CGRP-receptor antagonists—a fresh approach to migraine therapy? *N Engl J Med.* 2004; 350(11):1073-1075.

Edmeads J, Findlay H, Tugwell P, Pryse-Phillips W, Nelson R F, Murray T J. Impact of migraine and tension-type headache on life-style, consulting behaviour, and medication use: a Canadian population survey. *Can J Neurol Sci.* 1993; 20(2):131-137.

Evers S, Afra J, Frese A, Goadsby P J, Linde M, May A, Sindor P S; European Federation of Neurological Societies. EFNS guideline on the drug treatment of migraine—revised report of an EFNS task force. *Eur J Neurol.* 2009; 16(9):968-981.

Fenton B W, Palmieri P, Diantonio G, Vongruenigen V. Application of Patient-Reported Outcomes Measurement Information System to chronic pelvic pain. *J Minim Invasive Gynecol.* 2011; 18(2):189-193.

Ferrari M D. The economic burden of migraine to society. *Pharmacoeconomics.* 1998; 13(6):667-676.

Ford J H, Jackson J, Milligan G, Cotton S, Ahl J, Aurora S K. A real-world analysis of migraine: a cross-sectional study of disease burden and treatment patterns. *Headache.* 2017; 57(10):1532-1544.

Fox A W, Davis R L. Migraine chronobiology. *Headache.* 1998; 38(6):436-441.

[GBD] Global Burden of Disease 2016 Disease and Injury Incidence and Prevalence Collaborators. Global, regional, and national incidence, prevalence, and years lived with disability for 328 diseases and injuries for 195 countries, 1990-2016: a systematic analysis for the Global Burden of Disease Study 2016. *Lancet.* 2017; 390(10100):1211-1259.

Gil-Gouveia R, Oliveira A G, Martins I P. The impact of cognitive symptoms on migraine attack-related disability. *Cephalalgia.* 2016; 36(5):422-430.

Goadsby P J, Lipton R B, Ferrari M D. Migraine—current understanding and treatment. *N Engl J Med.* 2002; 346 (4):257-270.

Gonzalez J M, Johnson F R, Runken M C, Poulos C M. Evaluating migraineurs' preferences for migraine treatment outcomes using a choice experiment. *Headache.* 2013; 53(10):1635-1650.

Guy W. ECDEU assessment manual for psychopharmacology. Rockville, MD: National Institute of Mental Health, Psychopharmacology Research Branch. 1976; p 217-222. Available at: https://archive.org/details/ecdeuassessmentm1933guyw. Accessed Jun. 10, 2019.

Hawkins K, Wang S, Rupnow M F. Indirect cost burden of migraine in the United States. *J Occup Environ Med.* 2007; 49(4):368-374.

HealthMeasures. PROMIS instrument development and validation: scientific standards, version 2.0. May 2013. Available at: http://www.healthmeasures.net/images/PROMIS/PROMISStandards_Vers2.0_Final.pdf. Accessed Jul. 12, 2019.

[HealthMeasures]. PROMIS Sleep Disturbance (PROMIS-SD). Available at: http://www.healthmeasures.net/explore-measurement-systems/promis/measure-development-research/validation. Accessed Jul. 12, 2019.

Hepp Z, Dodick D W, Varon S F, Gillard P, Hansen R N, Devine E B. Adherence to oral migraine-preventive medications among patients with chronic migraine. *Cephalalgia.* 2015; 35(6):478-488.

[IHS ICHD-3] Headache Classification Committee of the International Headache Society (IHS). The International Classification of Headache Disorders, 3rd edition. *Cephalalgia.* 2018; 38(1):1-211.

Jensen R E, King-Kallimanis B L, Sexton E, Reeve B B, Moinpour C M, Potosky A L, Lobo T, Teresi J A. Measurement properties of PROMIS sleep disturbance short forms in a large, ethnically diverse cancer cohort. *Psychol Test Assess Model.* 2016; 58(2):353-370.

Jhingran P, Davis S M, LaVange L M, Miller D W, Helms R W. MSQ: Migraine-Specific Quality-of-Life Questionnaire. Further investigation of the factor structure. *Pharmacoeconomics.* 1998a; 13(6):707-717.

Jhingran P, Osterhaus J T, Miller D W, Lee J T, Kirchdoerfer L. Development and validation of the Migraine-Specific Quality of Life Questionnaire. *Headache.* 1998b; 38(4): 295-302.

Kenward M G, Roger J H. Small sample inference for fixed effects from restricted maximum likelihood. *Biometrics.* 1997; 53(3):983-997.

Kroenke K, Spitzer R L, Williams J B. The PHQ-9: validity of a brief depression severity measure. *J Gen Intern Med.* 2001; 16(9):606-613.

Leonardi M, Raggi A, Ajovalasit D, Bussone G, D'Amico D. Functioning and disability in migraine. *Disabil Rehabil.* 2010; 32(Suppl 1):S23-S32.

Linde M, Dahlof C. Attitudes and burden of disease among self-considered migraineurs—a nation-wide population-based survey in Sweden. *Cephalalgia.* 2004; 24(6):455-465.

Lipton R B, Bigal M E, Diamond M, Freitag F, Reed M L, Stewart W F; AMPP Advisory Group. Migraine prevalence, disease burden, and the need for preventive therapy. *Neurology.* 2007; 68(5):343-349.

Lipton R B, Bigal M E, Ashina S, Burstein R, Silberstein S, Reed M L, Serrano D, Stewart W F; American Migraine Prevalence Prevention Advisory Group. Cutaneous allodynia in the migraine population. *Ann Neurol.* 2008; 63(2):148-158.

Loder E, Biondi D. General principles of migraine management: the changing role of prevention. *Headache.* 2005; 45(suppl 1): S33-S47.

Loder E W, Rizzoli P. Tolerance and loss of beneficial effect during migraine prophylaxis: clinical considerations. *Headache.* 2011; 51(8):1336-1345.

Mansfield C, Gebben D J, Sutphin J, Tepper S J, Schwedt T J, Sapra S, Shah N. Patient preferences for preventive migraine treatments: a discrete-choice experiment. *Headache.* 2019; 59(5):715-726.

Martelletti P. The therapeutic armamentarium in migraine is quite elderly. *Expert Opin Drug Metab Toxicol.* 2015; 11(2):175-177.

Martin B C, Pathak D S, Sharfman M I, Adelman J U, Taylor F, Kwong W J, Jhingran P. Validity and reliability of the Migraine-Specific Quality of Life Questionnaire (MSQ Version 2.1). *Headache.* 2000; 40(3):204-215.

Messali A, Sanderson J C, Blumenfeld A M, Goadsby P J, Buse D C, Varon S F, Stokes M, Lipton R B. Direct and indirect costs of chronic and episodic migraine in the United States: a web-based survey. *Headache.* 2016; 56(2):306-322.

Michel P, Dartigues J F, Lindoulsi A, Henry P. Loss of productivity and quality of life in migraine sufferers among French workers: results from the GAZEL cohort. *Headache.* 1997; 37(2):71-78.

Mitsikostas D D, Belesioti I, Arvaniti C, Mitropoulou E, Deligianni C, Kasioti E, Constantinidis T, Dermitzakis M, Vikelis M; Hellenic Headache Society. Patients' preferences for headache acute and preventive treatment. *J Headache Pain.* 2017; 18(1):102.

[MRF] Migraine Research Foundation. Migraine Facts. 2017. Available at: http://migraineresearchfoundation.org/about-migraine/migraine-facts/. Accessed Jun. 15, 2017.

Raporport A. How to Choose a Preventive Medication for Migraine. American Headache Society Information for Health Care Professionals. 2018. Available at https://americanheadachesociety.org/wp-content/uploads/2018/

05/Alan_Rapoport_-_Migraine_Prevention_Medications.pdf. Accessed Jul. 12, 2019.
Sacco S, Kurth T. Migraine and the risk for stroke and cardiovascular disease. *Curr Cardiol Rep.* 2014; 16(9): 524.
Seo J G, Park S P. Validation of the Patient Health Questionnaire-9 (PHQ-9) and PHQ-2 in patients with migraine. *J Headache Pain.* 2015a; 16:65.
Seo J G, Park S P. Validation of the Generalized Anxiety Disorder-7 (GAD-7) and GAD-2 in patients with migraine. *J Headache Pain.* 2015b; 16:97.
Silberstein S D, Holland S, Freitag F, Dodick D W, Argoff C, Ashman E; Quality Standards Subcommittee of the American Academy of Neurology; American Headache Society. Evidence-based guideline update: pharmacologic treatment for episodic migraine prevention in adults: report of the Quality Standards Subcommittee of the American Academy of Neurology and the American Headache Society. *Neurology.* 2012; 78(17):1337-1345.
Silberstein S D. Preventive migraine treatment. *Continuum (Minneap Minn.).* 2015; 21(4 Headache):973-989.
Speciali J G, Peres M, Bigal M E. Migraine treatment and placebo effect. *Expert Rev Neurother.* 2010; 10(3):413-419.
Spitzer R L, Kroenke K, Williams J B, Löwe B. A brief measure for assessing generalized anxiety disorder: the GAD-7. *Arch Intern Med.* 2006; 166(10):1092-1097.
Stachler R J, Schultz L R, Nerenz D, Yaremchuk K L. PROMIS evaluation for head and neck cancer patients: a comprehensive quality-of-life outcomes assessment tool. *Laryngoscope.* 2014; 124(6):1368-1376.
Woldeamanuel Y W, Cowan R P. Migraine affects 1 in 10 people worldwide featuring recent rise: A systematic review and meta-analysis of community-based studies involving 6 million participants. *J Neurol Sci.* 2017; 372:307-315.
Yu L, Buysse D J, Germain A, Moul D E, Stover A, Dodds N E, Johnston K L, Pilkonis P A. Development of short forms from the PROMIS™ sleep disturbance and Sleep-Related Impairment item banks. *Behav Sleep Med.* 2011; 10(1):6-24.

What is claimed:

1. A method for the prevention of migraine, in a patient in need thereof, comprising nightly administering to said patient 25-200 mg per oral dose of 2,4,6-trifluoro-N-[6-(1-methyl-piperidin-4-ylcarbonyl)-pyridin-2-yl]-benzamide, or a pharmaceutically acceptable salt thereof, at bedtime, for at least five consecutive nights.

2. The A method of claim 1, wherein 2,4,6-trifluoro-N-[6-(1-methyl-piperidin-4-ylcarbonyl)-pyridin-2-yl]-benzamide, or a pharmaceutically acceptable salt thereof, is orally administered nightly for at least thirty consecutive nights.

3. A method for the prevention of migraine, in a patient in need thereof, comprising nightly administering to said patient 25-200 mg per oral dose of 2,4,6-trifluoro-N-[6-(1-methyl-piperidin-4-ylcarbonyl)-pyridin-2-yl]-benzamide, or a pharmaceutically acceptable salt thereof, at bedtime, every other night for at least ten consecutive nights.

4. A method for the prevention of migraine, in a patient in need thereof, comprising nightly administering to said patient 25-200 mg per oral dose of 2,4,6-trifluoro-N-[6-(1-methyl-piperidin-4-ylcarbonyl)-pyridin-2-yl]-benzamide, or a pharmaceutically acceptable salt thereof, at bedtime, every other night for at least thirty consecutive nights.

5. A method of claim 1 for the prevention of migraine, in a patient in need thereof, comprising nightly administering to said patient 25 mg per oral dose of 2,4,6-trifluoro-N-[6-(1-methyl-piperidin-4-ylcarbonyl)-pyridin-2-yl]-benzamide, or a pharmaceutically acceptable salt thereof.

6. A method of claim 1 for the prevention of migraine, in a patient in need thereof, comprising nightly administering to said patient 50 mg per oral dose of 2,4,6-trifluoro-N-[6-(1-methyl-piperidin-4-ylcarbonyl)-pyridin-2-yl]-benzamide, or a pharmaceutically acceptable salt thereof.

7. A method of claim 1 for the prevention of migraine, in a patient in need thereof, comprising nightly administering to said patient 75 mg per oral dose of 2,4,6-trifluoro-N-[6-(1-methyl-piperidin-4-ylcarbonyl)-pyridin-2-yl]-benzamide, or a pharmaceutically acceptable salt thereof.

8. A method of claim 1 for the prevention of migraine, in a patient in need thereof, comprising nightly administering to said patient 100 mg per oral dose of 2,4,6-trifluoro-N-[6-(1-methyl-piperidin-4-ylcarbonyl)-pyridin-2-yl]-benzamide, or a pharmaceutically acceptable salt thereof.

9. A method of claim 1 for the prevention of migraine, in a patient in need thereof, comprising nightly administering to said patient 150 mg per oral dose of 2,4,6-trifluoro-N-[6-(1-methyl-piperidin-4-ylcarbonyl)-pyridin-2-yl]-benzamide, or a pharmaceutically acceptable salt thereof.

10. A method of claim 1 for the prevention of migraine, in a patient in need thereof, comprising nightly administering to said patient 200 mg per oral dose of 2,4,6-trifluoro-N-[6-(1-methyl-piperidin-4-ylcarbonyl)-pyridin-2-yl]-benzamide, or a pharmaceutically acceptable salt thereof.

\* \* \* \* \*

UNITED STATES PATENT AND TRADEMARK OFFICE
CERTIFICATE OF CORRECTION

PATENT NO. : 12,138,254 B2
APPLICATION NO. : 17/271950
DATED : November 12, 2024
INVENTOR(S) : Robert Russell Conley, Gudarz Davar and Kirk Willis Johnson Page 1 of 1

It is certified that error appears in the above-identified patent and that said Letters Patent is hereby corrected as shown below:

In the Claims

In the Claim 2, Column 74, Line 1: Delete "The A" and insert -- The --, therefor.

Signed and Sealed this
Nineteenth Day of August, 2025

Coke Morgan Stewart
*Acting Director of the United States Patent and Trademark Office*